US010456131B2

(12) United States Patent
Cheney et al.

(10) Patent No.: US 10,456,131 B2
(45) Date of Patent: Oct. 29, 2019

(54) METHOD AND APPARATUS FOR LOADING AND IMPLANTING A SHAPE MEMORY IMPLANT

(71) Applicant: BioMedical Enterprises, Inc., San Antonio, TX (US)

(72) Inventors: Daniel F. Cheney, San Antonio, TX (US); Joseph H. Taber, San Antonio, TX (US); Luke A. Perkins, Bulverde, TX (US); Joseph P. Ritz, San Antonio, TX (US)

(73) Assignee: BioMedical Enterprises, Inc., San Antonio, TX (US)

( * ) Notice: Subject to any disclaimer, the term of this patent is extended or adjusted under 35 U.S.C. 154(b) by 516 days.

(21) Appl. No.: 14/950,321

(22) Filed: Nov. 24, 2015

(65) Prior Publication Data
US 2016/0074037 A1    Mar. 17, 2016

Related U.S. Application Data

(63) Continuation of application No. 14/271,563, filed on May 7, 2014, now Pat. No. 9,585,656.
(Continued)

(51) Int. Cl.
*A61F 2/46*  (2006.01)
*A61B 17/064* (2006.01)
(Continued)

(52) U.S. Cl.
CPC ...... *A61B 17/0642* (2013.01); *A61B 17/0684* (2013.01); *A61B 2017/00867* (2013.01); *A61B 2017/0645* (2013.01); *Y10T 29/49826* (2015.01)

(58) Field of Classification Search
CPC combination set(s) only.
See application file for complete search history.

(56) References Cited

U.S. PATENT DOCUMENTS 1,106,241 A   8/1914   Richardson
2,544,492 A   3/1947   Downing
(Continued)

FOREIGN PATENT DOCUMENTS

EP   0682920 A1   2/1995
EP   0857462 A1   1/1998
(Continued)

OTHER PUBLICATIONS

International Search Report and Written Opinion of the International Searching Authority dated Feb. 4, 2016 for PCT Application No. PCT/US2015/062902, filed Nov. 30, 2015.
(Continued)

*Primary Examiner* — Sameh Boles
(74) *Attorney, Agent, or Firm* — Christopher L. Makay

(57) ABSTRACT

An implant insertion device is adapted for use with a shape memory implant. The shape memory implant includes a bridge interconnecting first and second legs. The shape memory implant is movable between a first shape in which the first and second legs are substantially non-parallel and a second shape in which the first and second legs are substantially parallel. The implant insertion device engages the shape memory implant to maintain the shape memory implant in its second shape until the delivery of the shape memory implant into tissue or bone.

17 Claims, 18 Drawing Sheets

Related U.S. Application Data

(60) Provisional application No. 62/086,381, filed on Dec. 2, 2014.

(51) Int. Cl.
*A61B 17/068* (2006.01)
*A61B 17/00* (2006.01)

(56) References Cited

U.S. PATENT DOCUMENTS

| | | | |
|---|---|---|---|
| 3,939,828 A | 2/1976 | Mohr et al. | |
| 3,960,147 A | 6/1976 | Murray | |
| 4,269,180 A | 5/1981 | Dall et al. | |
| 4,438,769 A | 3/1984 | Pratt et al. | |
| 4,485,816 A | 12/1984 | Krumme | |
| 4,526,174 A | 7/1985 | Froehlich | |
| 4,570,623 A | 2/1986 | Ellison et al. | |
| 4,592,346 A | 6/1986 | Jurgutis | |
| 4,608,972 A | 9/1986 | Small | |
| 4,665,906 A | 5/1987 | Jervis | |
| 4,713,077 A | 12/1987 | Small | |
| 4,869,243 A | 9/1989 | Huene | |
| 5,067,957 A | 11/1991 | Jervis | |
| 5,112,336 A | 5/1992 | Krevolin et al. | |
| 5,163,557 A | 11/1992 | Sokolowski | |
| 5,171,252 A | 12/1992 | Friedland | |
| 5,246,443 A | 9/1993 | Mai | |
| 5,357,732 A | 10/1994 | Markle et al. | |
| 5,425,489 A | 6/1995 | Shichman et al. | |
| 5,474,557 A | 12/1995 | Mai | |
| 5,478,354 A | 12/1995 | Tovey et al. | |
| 5,769,856 A | 6/1998 | Dong et al. | |
| 5,779,707 A | 7/1998 | Bertholet et al. | |
| 5,785,713 A | 7/1998 | Jobe | |
| 5,976,159 A | 11/1999 | Bolduc et al. | |
| 6,001,110 A | 12/1999 | Adams | |
| 6,187,009 B1 | 2/2001 | Herzog et al. | |
| 6,268,589 B1 | 7/2001 | Flot | |
| 6,323,461 B2 | 11/2001 | Flot | |
| 6,412,639 B1 | 7/2002 | Hickey | |
| 6,607,542 B1 | 8/2003 | Wild | |
| 6,685,708 B2 | 2/2004 | Monassevitch et al. | |
| 6,783,531 B2 | 8/2004 | Allen | |
| 6,827,723 B2 | 12/2004 | Carson | |
| 7,240,677 B2 | 7/2007 | Fox | |
| 7,344,539 B2 | 3/2008 | Serhan et al. | |
| 7,428,807 B2 | 9/2008 | Vander Bush et al. | |
| 7,556,647 B2 | 7/2009 | Drews et al. | |
| 7,678,115 B2 | 3/2010 | D'Alessio et al. | |
| 7,867,265 B2 | 1/2011 | Beutter | |
| 8,057,490 B2 | 11/2011 | Harris | |
| 8,114,138 B2 | 2/2012 | Nehls | |
| 8,118,952 B2 | 2/2012 | Gall et al. | |
| 8,137,351 B2 | 3/2012 | Prandi | |
| 8,191,220 B2 | 6/2012 | Magnuson et al. | |
| 8,211,109 B2 | 7/2012 | Groiso | |
| D669,984 S | 10/2012 | Cheney et al. | |
| D669,985 S | 10/2012 | Cheney et al. | |
| D676,962 S | 2/2013 | Cheney et al. | |
| 8,584,853 B2 | 11/2013 | Knight et al. | |
| 8,596,514 B2 | 12/2013 | Miller et al. | |
| 9,585,656 B2 | 3/2017 | Taber et al. | |
| 9,855,036 B2 | 1/2018 | Palmer et al. | |
| 9,931,115 B2 | 4/2018 | Morgan et al. | |
| 2004/0097970 A1 | 5/2004 | Hughett | |
| 2005/0033430 A1 | 2/2005 | Powers et al. | |
| 2005/0043757 A1 | 2/2005 | Arad et al. | |
| 2005/0080454 A1 | 4/2005 | Drews | |
| 2005/0009660 A1 | 5/2005 | Allen | |
| 2005/0107807 A1 | 5/2005 | Nakao | |
| 2005/0113832 A1 | 5/2005 | Molz et al. | |
| 2005/0143749 A1 | 6/2005 | Zalenski et al. | |
| 2006/0106388 A1 | 5/2006 | Lococo | |
| 2006/0229627 A1 | 10/2006 | Hunt et al. | |
| 2007/0118141 A1 | 5/2007 | Marchyn et al. | |
| 2007/0118224 A1 | 5/2007 | Shah et al. | |
| 2008/0065153 A1 | 3/2008 | Allard et al. | |
| 2008/0110957 A1 | 5/2008 | McBride et al. | |
| 2008/0319443 A1 | 12/2008 | Focht et al. | |
| 2009/0062800 A1 | 3/2009 | Shano | |
| 2009/0062806 A1 | 3/2009 | Scott et al. | |
| 2009/0216285 A1 | 8/2009 | Ek et al. | |
| 2009/0272786 A1 | 11/2009 | Zeiner et al. | |
| 2010/0133316 A1 | 6/2010 | Lizee et al. | |
| 2010/0191258 A1 | 7/2010 | Harris et al. | |
| 2010/0217270 A1 | 8/2010 | Polinski et al. | |
| 2011/0093018 A1 | 4/2011 | Prasad et al. | |
| 2011/0186456 A1 | 8/2011 | Bertazzoni et al. | |
| 2011/0270327 A1 | 11/2011 | Blakemore et al. | |
| 2012/0024937 A1 | 2/2012 | Allen | |
| 2012/0085809 A1 | 4/2012 | Milo | |
| 2012/0209305 A1 | 8/2012 | Deodhar et al. | |
| 2012/0209401 A1* | 8/2012 | Euteneuer | A61F 2/0063 623/23.72 |
| 2012/0228355 A1 | 9/2012 | Combrowski et al. | |
| 2012/0259419 A1 | 10/2012 | Brown et al. | |
| 2013/0026206 A1 | 1/2013 | Fox | |
| 2013/0026207 A1 | 1/2013 | Fox | |
| 2013/0030437 A1 | 1/2013 | Fox | |
| 2013/0030438 A1 | 1/2013 | Fox | |
| 2013/0184476 A1 | 7/2013 | McIff et al. | |
| 2013/0231667 A1 | 9/2013 | Taylor et al. | |
| 2014/0018809 A1 | 1/2014 | Allen | |
| 2014/0097228 A1 | 4/2014 | Taylor et al. | |
| 2014/0175157 A1 | 6/2014 | Vold et al. | |
| 2014/0276830 A1 | 9/2014 | Cheney | |
| 2014/0277516 A1 | 9/2014 | Miller et al. | |
| 2014/0358187 A1 | 12/2014 | Taber et al. | |
| 2015/0133940 A1 | 5/2015 | Palmer et al. | |
| 2015/0257801 A1 | 9/2015 | Palmer et al. | |
| 2016/0015384 A1 | 1/2016 | Roedl et al. | |
| 2016/0066907 A1 | 3/2016 | Cheney et al. | |
| 2016/0074037 A1 | 3/2016 | Cheney et al. | |
| 2016/0235460 A1 | 8/2016 | Wahl | |
| 2017/0000482 A1 | 1/2017 | Averous et al. | |
| 2017/0065275 A1 | 3/2017 | Cheney | |
| 2017/0281157 A1 | 10/2017 | Hartdegen et al. | |

FOREIGN PATENT DOCUMENTS

| | | | |
|---|---|---|---|
| EP | 0826340 A2 | 3/1998 | |
| EP | 1870042 A1 | 12/2007 | |
| FR | 2874166 A1 | 2/2006 | |
| WO | 1992017122 A2 | 10/1992 | |
| WO | 2008129061 A1 | 10/2008 | |
| WO | 2010004330 A1 | 1/2010 | |
| WO | 2013055824 A1 | 4/2013 | |

OTHER PUBLICATIONS

4-Fusion Shape Memory Implant Training Slide Images, Memometal, Inc., 2008.
4-Fusion Shape Memory Implant Brochure, Memometal, Inc., Jun. 23, 2009.
MemoGraph Brochure, M.B.A. (Memory Biological Application), Parc Club de Nancy de Brabois,Batiment B11, 4 allee Vincennes, 54500 Vandceurve, France, 1999.
OSStaple Brochure Including pictures of staple loaded in shipping block, BioMedical Enterprises, Inc., 14875 Omicron Drive, Suite 205, San Antonio, TX 78245, 2010.
E. A. Van Amerongen et al., "Four-Corner Arthrodesis Using the Quad Memory Staple," Journal of Hand Surgery (European vol. 2008) (Jan. 7, 2009).
U. Rethnam et al., "Mechanical Characteristics of Three Staples Commonly Used in Foot Surgery," Journal of Foot and Ankle Research (Feb. 25, 2009) available at http://www.jfootankleres.com/content/2/1/5.
T. F. Smith, "The Bone Staple: Tried and True Superhero of Bone Fixation," Educational Materials Update Chapter 41 (2010) available at www.podiatryinstitute.com/pdfs/Update 2010/2010 41.pdf.
Elevest Procedure Kit, Instructions for Use by CooperSurgical (©2007).

(56) References Cited

OTHER PUBLICATIONS

Agee WristJack, Surgeon's Manual by Hand BioMechanics Labs, Inc. (©1990-2002).
Development of a Nickel-Titanium Shape Memory Alloy Bone Repair Staple and Other In-Vivo Orthopaedic and Cardio-Vascular Devices, A.W. Anson, D.H.R. Jenkins, and S. Andrews, Proceedings of the Technology Transfer Workshop, Held at ESA/ESTEC Noordwijk, The Netherlands, May 1994 (ESA SP-364, Aug. 1994).
Superelastic Fixation System Brochure, Memometal Inc., USA, Aug. 12, 2009.
Shape Memory Staple System for Arthrodesis and Skeletal Fixation of the Hand Brochure, Core Essence Orhtopaedics, Inc., 2009.
ENTact™ Septal Stapler, Product brochure by ENTrigue Surgical, Inc. (©2009).
R. M. Sloan et al., "Orthopedic Fixation Devices," Radiographics at 823 (Sep. 1991).
J. Arthur, "Improving Operating Efficiency in Five Days," Lean Six Sigma for Hospitals, McGraw-Hill (2011).
K. Yamauchi et al. (ed.), "Shape Memory and Superelastic Alloys: Applications and Technologies" (2011).
BioResearch Innovations (BRI), "Memodyn Compression Staple," FDA 510(K) disclosure (Jan. 2004).
G. C. Taylor et al., "Complications of Internal Fixation," Podiatry Institute Educational Materials Update Chapter 79 (1992).
Wright Medical Technology, Inc., "Charlotte Compression Staple as described by Robert Anderson, MD; Bruce Cohen, MD; and W. Hodges Davis, MD" (2007).
A. A. Weinbroum et al., "Efficiency of the Operating Room Suite," American Journal of Surgery 244-250 (2003).
G. G. Porto, "Safety by Design: Ten Lessons From Human Factors Research," Journal of Healthcare Risk Management 43-50 (Fall 2011).
European Patent Office Search Report for EP15865387.3, Jun. 12, 2018, EP Application Counterpart to U.S. Appl. No. 14/944,710.
Russell, Scott M., Design Considerations for Nitinol Bone Staples, Journals of Materials Engineering and Performance, vol. 18(5-6), Aug. 2009, USA.
Petition for Inter Partes Review (IPR No. 2015-00786), Wright Medical Technology, Inc., *Petitioner*, v. *BioMedical Enterprises, Inc.*, Patent Owner, U.S. Pat. No. 8,584,853 issued to Knight et al., Filed Feb. 20, 2015.
Declaration in Support of Petition for Inter Partes Review (IPR No. 2015-00786), Wright Medical Technology, Inc., *Petitioner*, v. *BioMedical Enterprises, Inc.*, Patent Owner, U.S. Pat. No. 8,584,853 issued to Knight et al., Filed Feb. 20, 2015.

\* cited by examiner

METHOD AND APPARATUS FOR LOADING AND IMPLANTING A SHAPE MEMORY IMPLANT

BACKGROUND OF THE INVENTION

1. Field of the Invention

The present invention relates generally to an implantation device and, more particularly, but not way of limitation, to an implantation device designed for loading with a surgical implant and for subsequent delivery of the surgical implant. The implantation device uses jaws and a slider to secure a surgical implant and allow implantation into a patient.

2. Description of the Related Art

Shape memory implants are commonly used in surgical procedures that require the reattachment or fusing of tissue or bone. Shape memory implants can be composed of shape memory material such as Nitinol that allows the shape memory implants to have a first final shape and the ability to transform into a second shape. A shape memory implant can be either thermally activated, in which an external heating source or body temperature would be required to activate the implant, or mechanically activated, in which a constraining instrument would be required. A shape memory implant that requires mechanical constraint stores mechanical energy due to elastic (recoverable) deformation, and then releases the stored mechanical energy when the constraint is removed. In these types of implants, the implants are mechanically deformed into their second shape and maintained in their second shape by instrumentation such that, upon release from the instrumentation, the implants elastically deform from their second shape into their first final shape.

In surgical procedures, the elastic property of constrained shape memory implants is used as follows. Bones that require fixating are aligned, and the shape memory implant, which has been mechanically deformed to its second shape, is maintained in instrumentation and inserted between the bones. In the second shape, the legs of the implant are generally parallel. After insertion, the shape memory implant is released from the instrumentation, whereupon the shape memory implant elastically returns to its first final shape such that the shape memory implant maintains the bones fixated together. In the first final shape, the legs of the implant are converging at the tips. Because the shape memory implant stores mechanical energy, it continuously applies force to the fixated bones as the shape memory implant transitions from the second shape to the first final shape, which aids in the healing process.

Various types of instrumentation can be used for either maintaining the shape memory implants in their second shape or moving an implant from its first final shape to a temporary second shape. Some companies used metal forceps to open and insert the shape memory implant. These forceps have to be sterilized by a hospital, and then a shape memory implant can be placed on the forceps, opened to a desired position, and used for inserting the implant. Although potentially effective, forceps require the implant to be loaded into the forceps during surgery, which might be cumbersome and time consuming. In addition, forceps might be large which could hinder implantation of the shape memory implant into a patient during surgery. It is also possible that a physician using the forceps might damage the shape memory implant in various ways, such as stretching the implant beyond the second shape, fatiguing the implant, or causing metal-on-metal scraping of the implant with the instrument. Furthermore, forceps can be expensive instruments that require cleaning and sterilization after each surgery.

Other companies use plastic and disposable tools to maintain a shape memory implant in the second shape. This type of instrumentation can be preloaded and sterilized with the implant already in the second shape, and the implant can be pre-activated so that it does not require heating with an external heater or body temperature after use. One type of plastic and disposable instrument operates by having the implant fit inside a passage that is substantially the same diameter as the shape memory implant. By using this method, the implant insertion device allows the shape memory implant to be preloaded prior to surgery. However, using an implant insertion device that substantially conforms to the profile of the shape memory implant can create several problems for a surgeon. First, this type of implant insertion device often makes disengagement of the shape memory staple after implantation problematic. In particular, the shape memory implant sticks to the implant insertion device due to the frictional engagement between the shape memory implant, which is trying to compress, and the passage of the implant insertion device, resulting in a more difficult surgical procedure and the potential for a less than satisfactory fixation of tissue or bone. Second, this type of implant insertion device results in an abrupt and sudden release of stored mechanical energy as the implant is removed from the device. This type of implant insertion device provides no method by which to slowly transition the stored energy in the implant from the implant insertion device to the bones that are being fixated. Finally, this type of implant insertion device can result in entanglement during release, in which the implant legs begin to compress upon release and make extraction of this type of insertion device more difficult.

Accordingly, an instrument that constrains a shape memory implant in its second shape, allows the shape memory implant to be preloaded and sterilized prior to surgery, simplifies removal of the shape memory implant after partial implantation, and controls the rate of release of tension would be beneficial.

SUMMARY OF THE INVENTION

In accordance with the present invention, an implant insertion system includes a shape memory implant and an implant insertion device adapted for use with the shape memory implant. The shape memory implant is movable between a first shape and a second shape. In particular, the shape memory implant includes a bridge interconnecting first and second legs. The first and second legs are substantially non-parallel when the shape memory implant resides in its first shape, and the first and second legs are substantially parallel when the shape memory implant resides in its second shape. The implant insertion device maintains the shape memory implant in the second shape until the implant insertion device is used to deliver the shape memory implant into tissue or bone.

The implant insertion device includes a body having a slider receiver and a handle that allows manipulation of the implant insertion device and delivery of the shape memory implant into tissue or bone. The body includes a first arm terminating in a first jaw adapted to engage the shape memory implant and a second arm terminating in a second jaw adapted to engage the shape memory implant. The body further includes third and fourth arms terminating in a third jaw adapted to engage the shape memory implant. The first, second, and third jaws are movable from a disengaged position to an engaged position. The first arm may be shorter in length than the second arm such that the implant insertion device is adapted to receive a shape memory implant with a first bridge at a height different from a second bridge.

The implant insertion device further includes a slider coupled with the slider receiver of the body. The slider is movable between an unlocked position and a locked position. In its locked position, the slider inserts between the first jaw and the second jaw and maintains the first and second jaws in their engaged positions. The slider in its locked position further engages the third jaw and maintains the third jaw in its engaged position with the first and second jaws such that the first, second, and third jaws engage and maintain the shape memory implant in its second shape. In particular, when the first, second, and third jaws reside in their engaged positions, the first jaw engages and maintains the first leg in its substantially parallel second shape, the second jaw engages and maintains the second leg in its substantially parallel second shape, and the third jaw abuts the first and second jaws such that a portion of the third jaw inserts between the first and second jaws.

After the implant insertion device delivers the shape memory implant into tissue or bone, the slider is moved from its locked position to its unlocked position. In its unlocked position, the slider releases from the first, second, and third jaws, which permits the first, second, and third jaws to move from their engaged positions to their disengaged positions. In their disengaged positions, the first, second, and third jaws disengage from the shape memory implant, thereby releasing the shape memory implant and allowing the shape memory implant to move from its second shape to its first shape.

The first jaw experiences a rotation relative to the first arm and the second jaw experiences a rotation relative to the second arm when the slider is moved from its unlocked to its locked position. Consequently, the first jaw and the second jaw rotate away from the shape memory implant when the slider is moved from its locked to its unlocked position. In particular, the first arm maintains the first jaw canted downward and the second arm maintains the second jaw canted downward when the slider resides in its unlocked position. As such, insertion of the slider to its locked position between the first and second jaws moves the first and second jaws horizontally outward and in an upward arc to their engaged positions such that the first and second jaws engage the shape memory implant and maintain the shape memory implant in the second shape.

The first jaw includes a tooth having a leg interface that abuts the first leg of the shape memory implant then the first jaw resides in its engaged position. Likewise, the second jaw includes a tooth having a leg interface that abuts a second leg of the shape memory implant when the second jaw resides in its engaged position. The third jaw abuts the first and second jaws when the first, second, and third jaws reside in their engaged positions. Moreover, the third jaw includes a tooth that inserts between the tooth of the first jaw and the tooth of the second jaw such that the tooth of the third jaw maintains the first jaw separated from the second jaw.

The first arm and the first jaw define a first channel that engages at least a portion of the bridge of the shape memory implant when the first jaw resides in its engaged position. Similarly, the second arm and the second jaw define a second channel that engages at least a portion of the bridge of the shape memory implant when the second jaw resides in its engaged position. Furthermore, the third and fourth arms and the third jaw define a third channel that engages at least a portion of the bridge of the shape memory implant when the third jaw resides in its engaged position.

The slider includes a slot adapted to receive therein the slider receiver of the body. The slot allows coupling of the slider with the body between the first and second arms and the third and fourth arms such that the slider remains coupled with the body during movement of the slider between its unlocked and locked positions. The slider further includes a clasp securable with slider channels in each of the first, second, and third jaws. The clasp maintains the slider engaged with the first, second, and third jaws when the slider resides in its locked position.

In a method of holding a shape memory implant until the delivery of the shape memory implant into tissue or bone, a shape memory implant is provided. The shape memory implant includes a bridge interconnecting first and second legs. The shape memory implant is movable between a first shape wherein the first and second legs are non-parallel and a second shape wherein the first and second legs are substantially parallel. The shape memory implant is moved into its second shape wherein the first and second legs are substantially parallel. The shape memory implant is placed between first and second jaws of the implant insertion device and a third jaw of the implant insertion device. A slider of an implant insertion device is moved whereby the slider inserts between the first and second jaws and engages the third jaw. The slider maintains the first and second jaws in their engaged positions such that the first jaw engages the first leg of the shape memory implant and the second jaw engages the second leg of the shape memory implant. The slider further maintains the third jaw in its engaged position with the first and second jaws such that the first, second, and third jaws engage and maintain the shape memory implant in its second shape wherein the first and second legs are substantially parallel.

Once the first, second, and third jaws are engaged to maintain the shape memory implant in its second shape wherein the first and second legs are substantially parallel, the implant insertion device is used to deliver into tissue or bone the shape memory implant in its second shape. The slider of the implant insertion device is moved whereby the slider disengages from the first, second, and third jaws. As a result, the third jaw disengages with the first and second jaws. In addition, the first jaw releases the first leg of the shape memory implant and the second jaw releases the second leg of the shape memory implant, thereby releasing the shape memory implant from the implant insertion device.

DETAILED DESCRIPTION OF THE PREFERRED EMBODIMENT

Figure 1A:
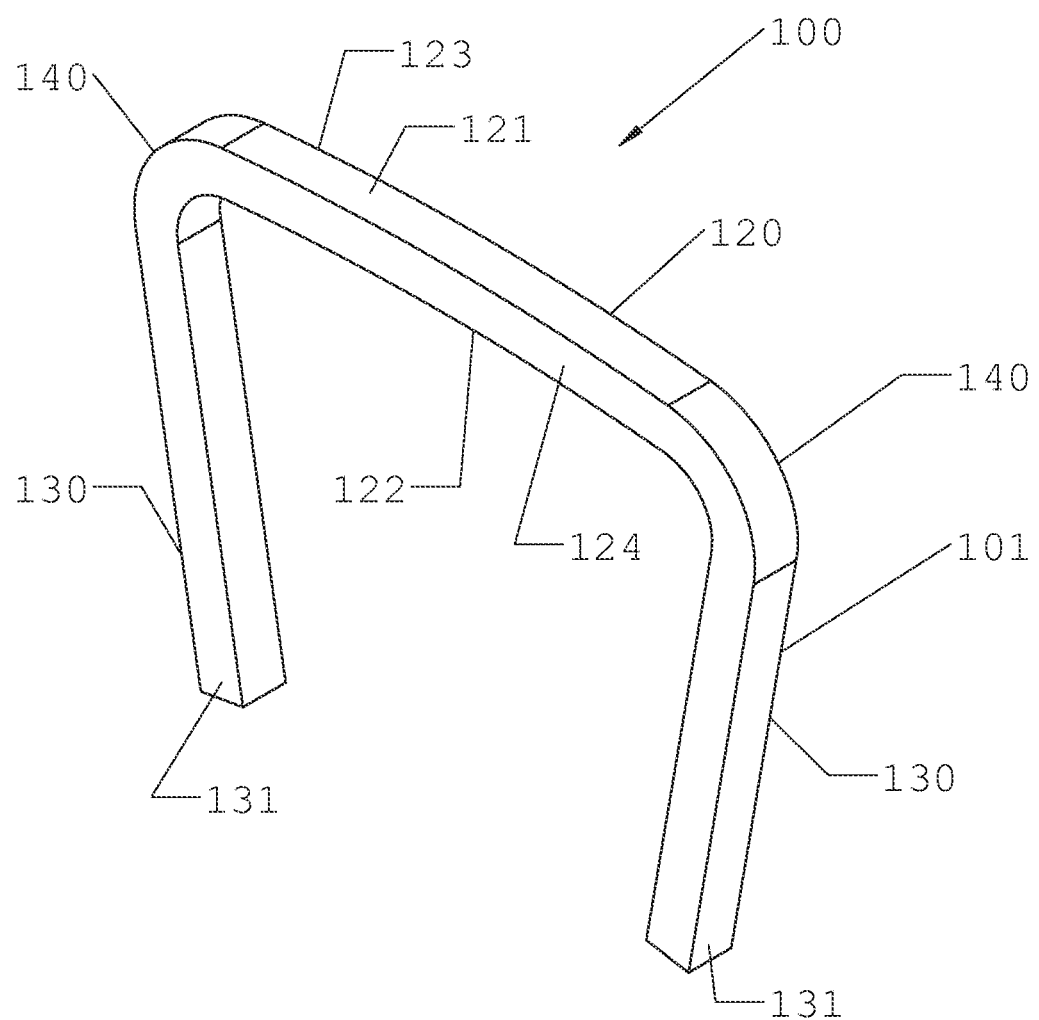
FIG. 1A is a perspective view of an implant in a first final shape for use with an implant insertion device according to a first embodiment.

As required, detailed embodiments of the present invention are disclosed herein; however, it is to be understood that the disclosed embodiments are merely exemplary of the invention, which may be embodied in various forms. Figures are not necessarily to scale, and some features may be exaggerated to show details of particular components or steps.

FIGS. 1A-3 illustrate a first embodiment of an implant insertion device 10 and an implant 100. The implant insertion device 10 secures the implant 100 to allow surgeon to insert the implant 100 into tissue or bone during surgery.

The implant 100 is a surgical staple and includes a bridge 120 and legs 130 formed integrally at corners 140. The bridge 120 further includes a top 121, a bottom 122, a back 123, and a front 124. The legs 130 further include tips 131 which may form a shape that is rounded for insertion into drill holes or the tips 131 may be pointed for impaction into bones. While the preferred embodiment discloses the implant 100 as a surgical staple, it should be understood by one of ordinary skill in the art that any implant such as a staple or plate adapted to engage and span bone such that the implant exerts a force, typically a compressive force, to the bone is suitable for the present invention.

Figure 1B:
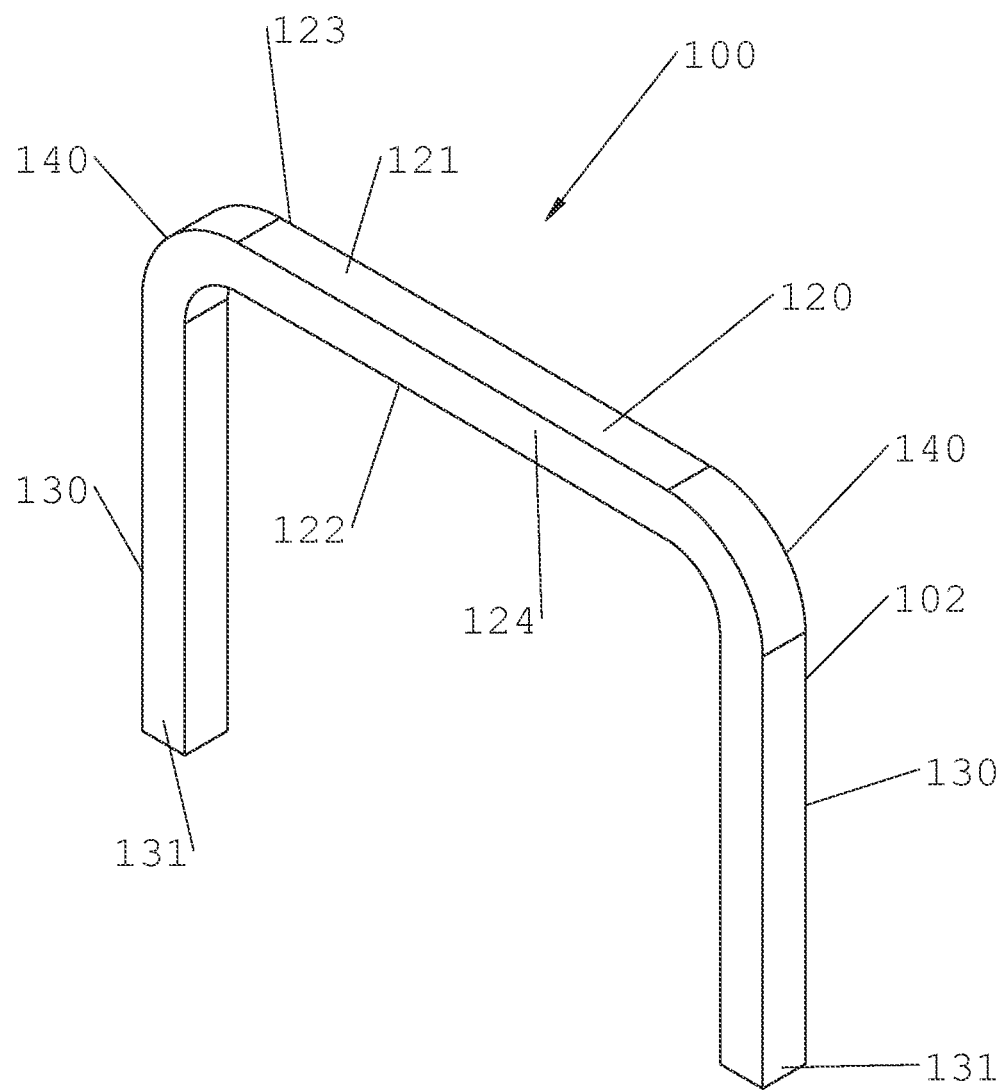
FIG. 1B is a perspective view of the implant in a second shape for use with the implant insertion device according to the first embodiment.

The implant 100 is composed of a shape memory material such as Nitinol that allows the implant 100 to have a first final shape 101 as illustrated in FIG. 1A and the ability to be elastically deformed into a second shape 102 as illustrated in FIG. 1B. The shape memory material gives the implant 100 elastic properties in that the implant 100 stores mechanical energy and is subject to elastic (recoverable) deformation when it releases the stored mechanical energy. The implant 100 is mechanically deformed into the second shape 102 and held in the second shape 102 by the implant insertion device 10 such that, upon release from the implant insertion device 10, the implant 100 elastically transforms from the second shape 102 into the first final shape 101.

The ability of the implant 100 to store mechanical energy and release that energy when it transitions from the second shape 102 to the first final shape 101 allows the implant 100 to fixate tissue or bone and to aid in the healing process. In particular, the implant 100, which has been mechanically deformed to its second shape 102, is held in implant insertion device 10 and inserted between tissue or bone that require fixating. After insertion, the implant 100 is removed from the implant insertion device 10, whereupon the implant 100 releases the stored mechanical energy by elastically deforming to the first final shape 101. This release of the stored mechanical energy by the implant 100 maintains the tissue or bone fixated together and aids in the healing process in that the implant 100 continuously applies force to the fixated tissue or bone as the implant 100 transitions from the second shape 102 to the first final shape 101.

The implant insertion device 10 includes a body 12 and a slider 30 that moves between an unlocked and a locked position. The implant insertion device 10 exists in either an implant disengagement position 11 (shown in FIG. 2) or an implant engagement position 13 (shown in FIG. 3) and is movable therebetween. In the implant disengagement position 11, the implant 100 slips in or out of position in the implant insertion device 10 with no obstruction. In the implant engagement position 13, the implant insertion device 10 engages the implant 100 and maintains the implant 100 in the second shape 102. In addition, the implant insertion device 10 allows a surgeon to manipulate the implant 100 and insert the implant 100 into tissue or bones that require fixating. The implant insertion device 10 can be made of any suitable material; however, in the first embodiment the implant insertion device 10 is made from plastic.

FIGS. 4-6B illustrate the body 12 of the implant insertion device 10. The body 12 of the implant insertion device 10 includes a slider receiver 8, a front 14, a back 16, a handle 18 having a top 15, arms 22 and 24, and arms 26 and 28. The slider receiver 8 is defined by flat grooves in the body 12 that receive a portion of the slider 30 to allow the securing of the slider 30 over the slider receiver 8 and thus to the body 12. The handle 18 provides a gripping surface on the front 14 and the back 16 of the body 12. The gripping surface of the handle 18 allows a surgeon to manipulate the implant insertion device 10 and therefore the implant 100 that is secured thereto. The arms 22 and 24 and the arms 26 and 28 attach to the handle 18 and include jaws 40 and a jaw 70, respectively. The jaws 40 and the jaw 70 move between a disengaged position and an engaged position. Furthermore, the arms 22 and 24 and the arms 26 and 28 form slider guides 27 and 29 respectively. The slider guides 27 and 29 allow the slider 30 to move between its unlocked and locked position.

In the preferred embodiment, the body 12 of the implant insertion device 10 is manufactured in one piece using a mold. However, the body 12 of the implant insertion device 10 could be manufactured in two separate pieces. In particular, the arms 22 and 24, the jaws 40, and a portion of the handle 8 form the first piece and the arms 26 and 28, the jaw 70, and a portion of the handle 18 form the second piece. These two pieces are fastened together using any suitable means such as a hinge or an adhesive to create the body 12.

The jaws 40 include teeth 41 that engage the implant 100 and the jaw 70 and slider channels 48 that engage the slider 30 as the slider 30 moves between its unlocked and its locked position. The teeth 41 include bridge interfaces 42 and leg interfaces 46 that engage the bridge 120 of the implant 100 as well as tooth interfaces 47 and jaw interfaces 49 that engage the jaw 70. Specifically, the bridge interfaces 42 and a portion of the arms 22 and 24 form a bridge channel 43 that receives a portion of the bridge 120 therein. Furthermore, the leg interfaces 46 engage the implant 100 such that the leg interfaces 46 abut the legs 130 of the implant 100 below the corners 140. The tooth interfaces 47 engage a portion of the jaw 70 that moves the jaws 40 from the disengaged position to the engaged position and aid in securing the implant 100 to the implant insertion device 10.

The jaw 70 includes a tooth 71 that engages the implant 100 and the jaws 40 and a slider channel 78 that engages the slider 30 as the slider 30 moves between its unlocked and its locked position. The tooth 71 includes a bridge interface 72 that engages the bridge 120 of the implant 100 and tooth interfaces 77 and jaw interfaces 79 that engage the jaws 40. The bridge interface 72 and a portion of the arms 26 and 28 form a bridge channel 73 that receives a portion of the bridge 120 therein.

Figure 7:
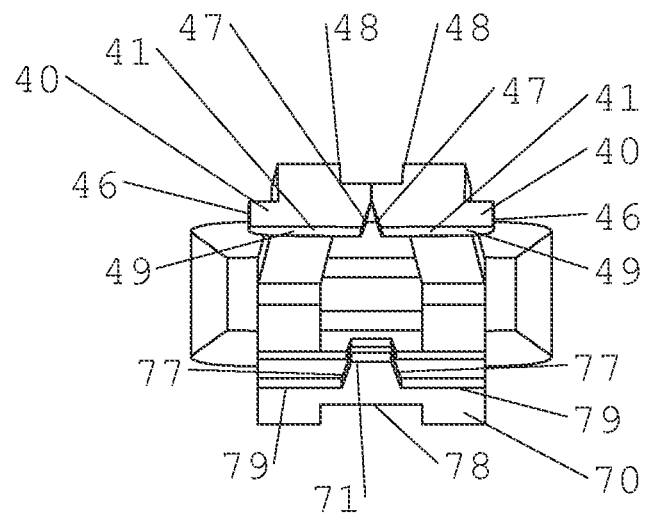
FIG. 7 is a front view illustrating the implant insertion device in the implant disengagement position.
Figure 8:
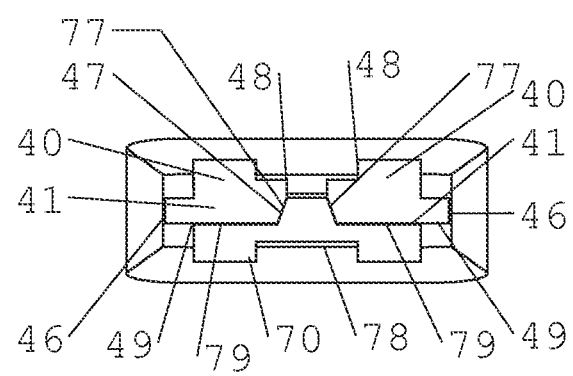
FIG. 8 is a front view illustrating the implant insertion device in the implant engagement position.

The jaws 40 and the jaw 70 move between the disengaged position and the engaged position to aid in the securing and removal of the implant 100. Specifically, as the implant insertion device 10 moves from its implant disengagement position 11 to its implant engagement position 13, the jaws 40 and the jaw 70 move from their disengaged position to their engaged position whereby the tooth interfaces 77 of the jaw 70 engage the tooth interfaces 47 of the jaw 40. As illustrated in FIGS. 7 and 8, the tooth interfaces 47 of the jaws 40 as well as the tooth interfaces 77 of the jaw 70 are beveled in order to aid in the securing and the removal of the implant 100 from the implant insertion device 10. In the first embodiment, the beveling of the tooth interfaces 47 of the jaws 40 and the tooth interfaces 77 of the jaw 70 reduces the normal force between contacting surfaces and thus the friction force between the jaws 40 and the jaw 70 as the implant insertion device 10 moves between its implant disengagement position 11 and its implant engagement position 13. The beveling of the of the tooth interfaces 47 of the jaws 40 and tooth interfaces 77 of the jaw 70 also creates a ramp that allows the jaw 70 to force open the jaws 40 similar to a wedge when the implant insertion device 10 moves from its disengagement position 11 to its implant engagement position 13. One of ordinary skill in the art will recognize that the angle of the bevel and application of trigonometry determines the friction force between the tooth interfaces 47 of the jaws 40 and the tooth interfaces 77 of the jaw 70. Reducing the amount of friction force between the tooth interfaces 47 of the jaws 40 and the tooth interfaces 77 of the jaw 70 aids in removing the implant 100 from the implant insertion device 10. Furthermore, the angle of the bevel also determines the force for separating the jaws 40 when the implant insertion device 10 moves from its implant disengagement position 11 to its implant engagement position 13.

Figure 2:
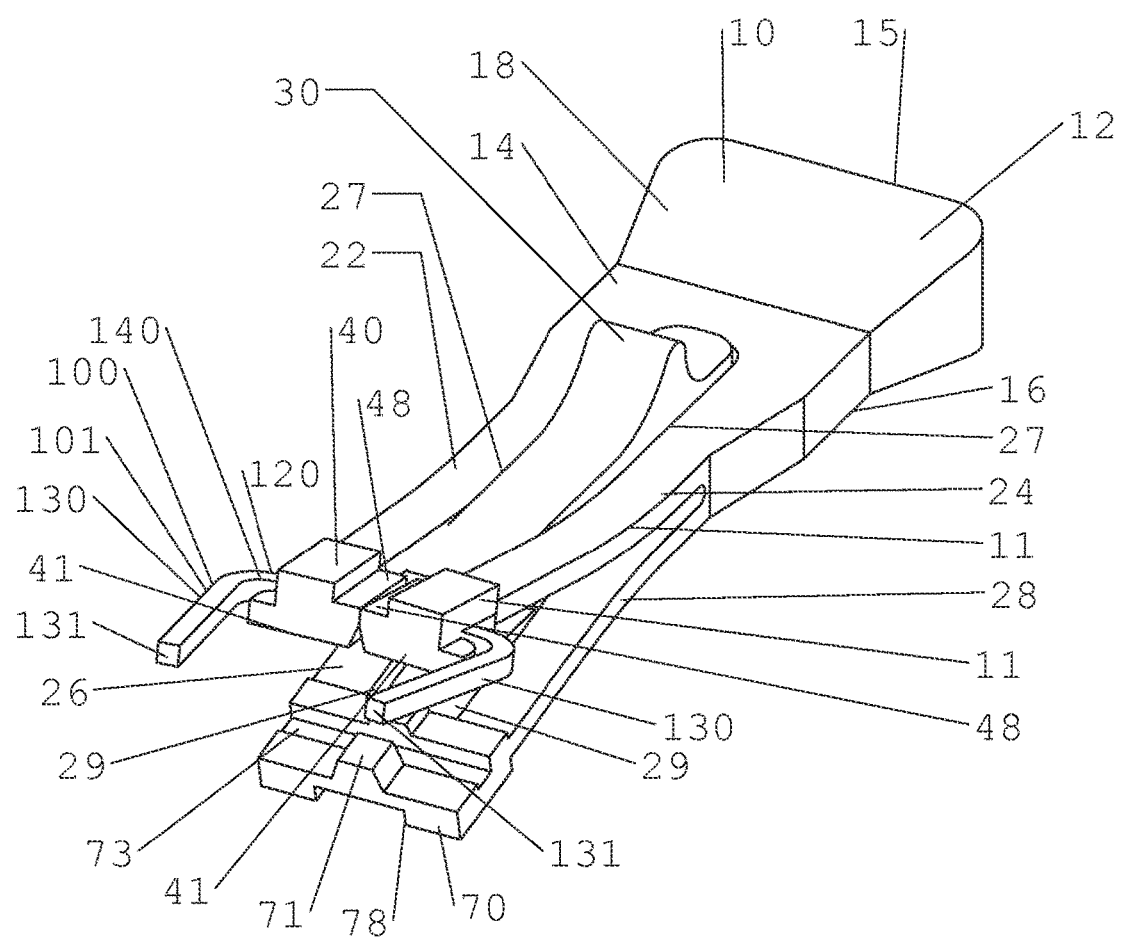
FIG. 2 is a perspective front view illustrating the implant and the implant insertion device in an implant disengagement position.
Figure 3:
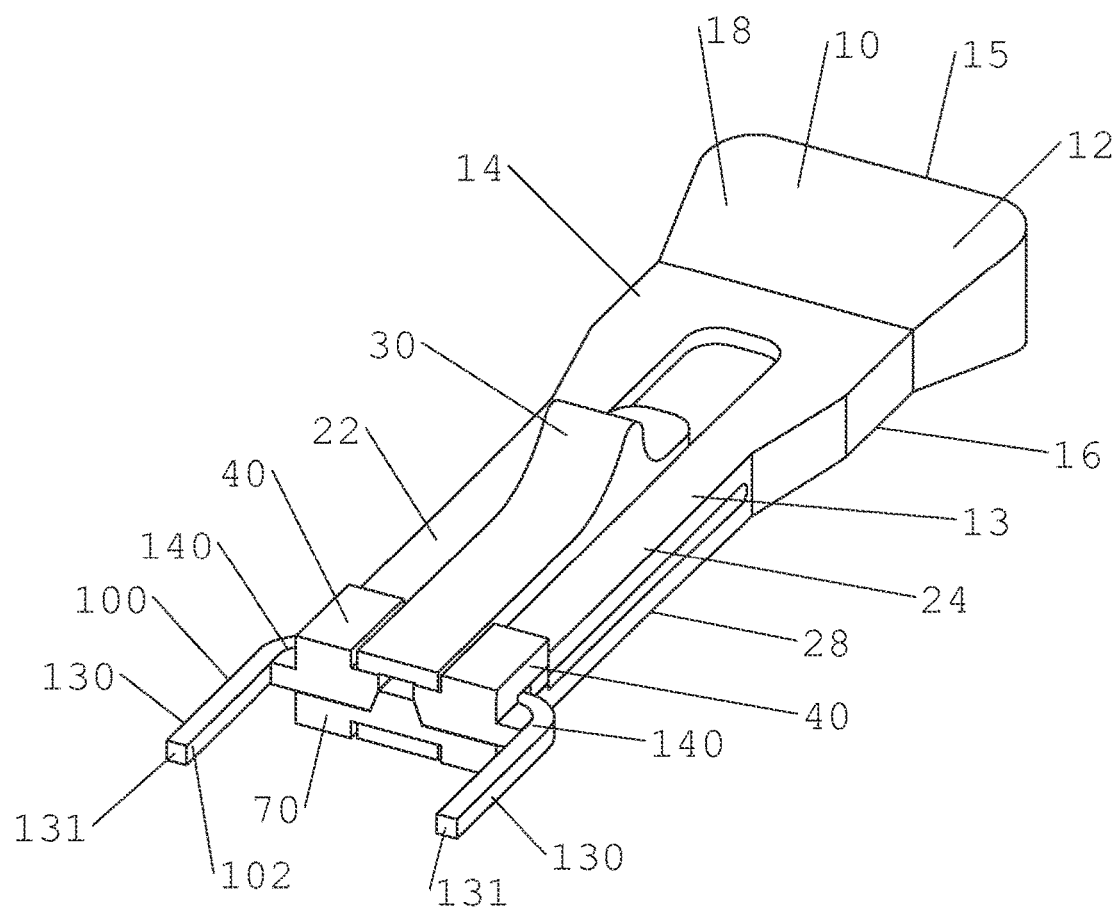
FIG. 3 is a perspective front view illustrating the implant and the implant insertion device in an implant engagement position.
Figure 4:
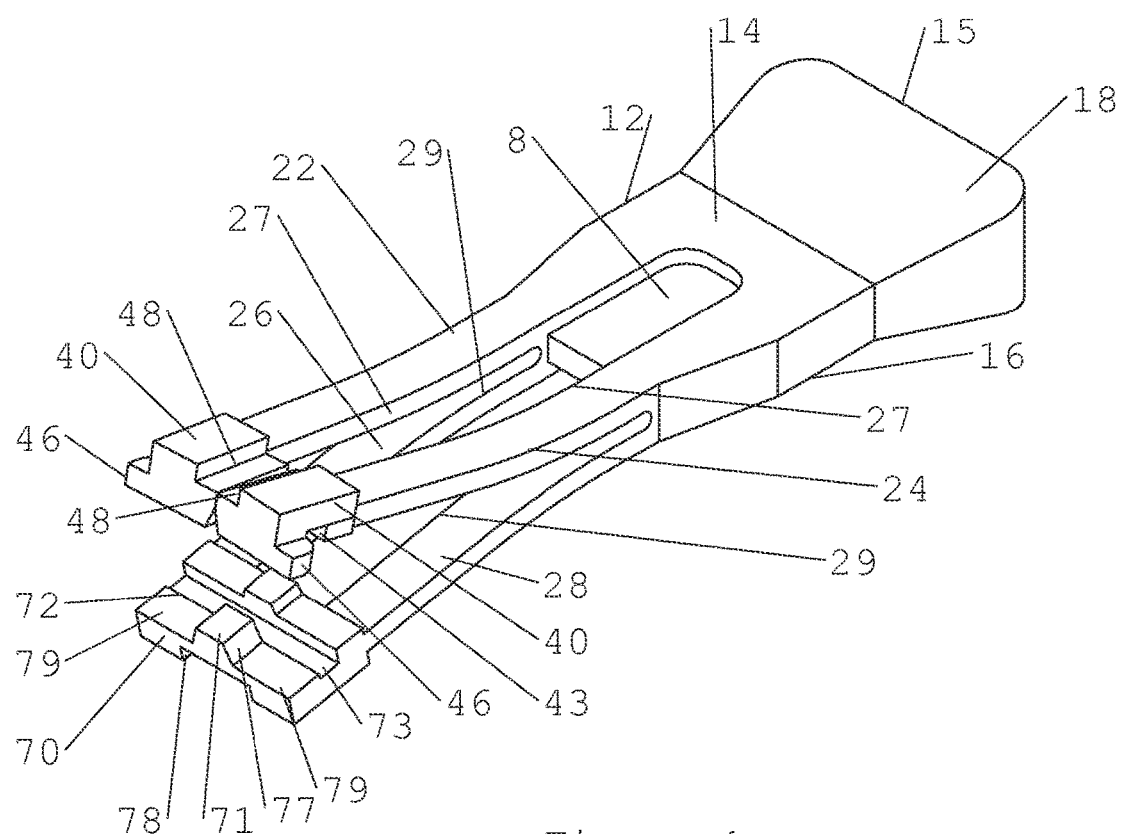
FIG. 4 is a perspective front view illustrating a body of the implant insertion device.
Figure 5A:
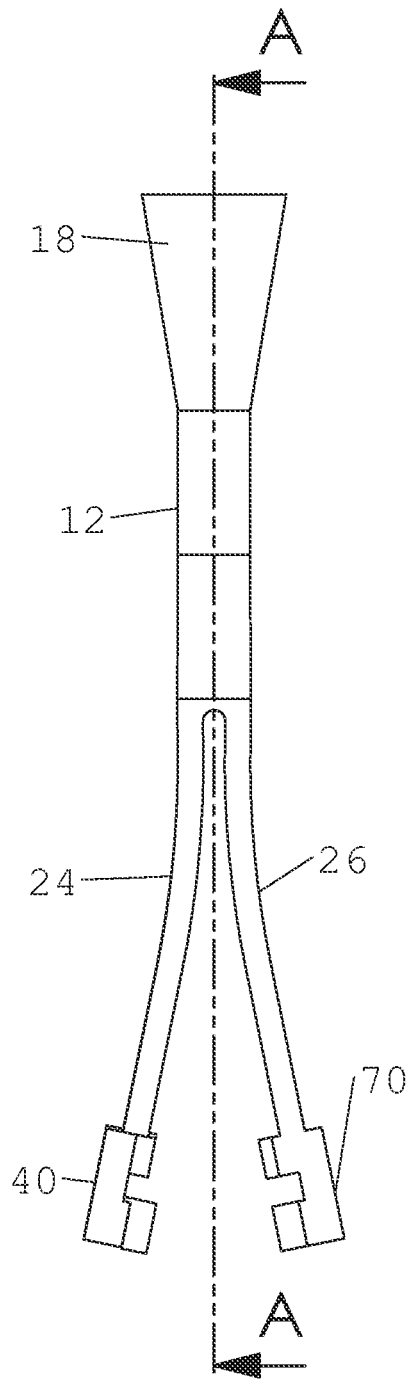
FIG. 5A is a side view illustrating the body of the implant insertion device.
Figure 5B:
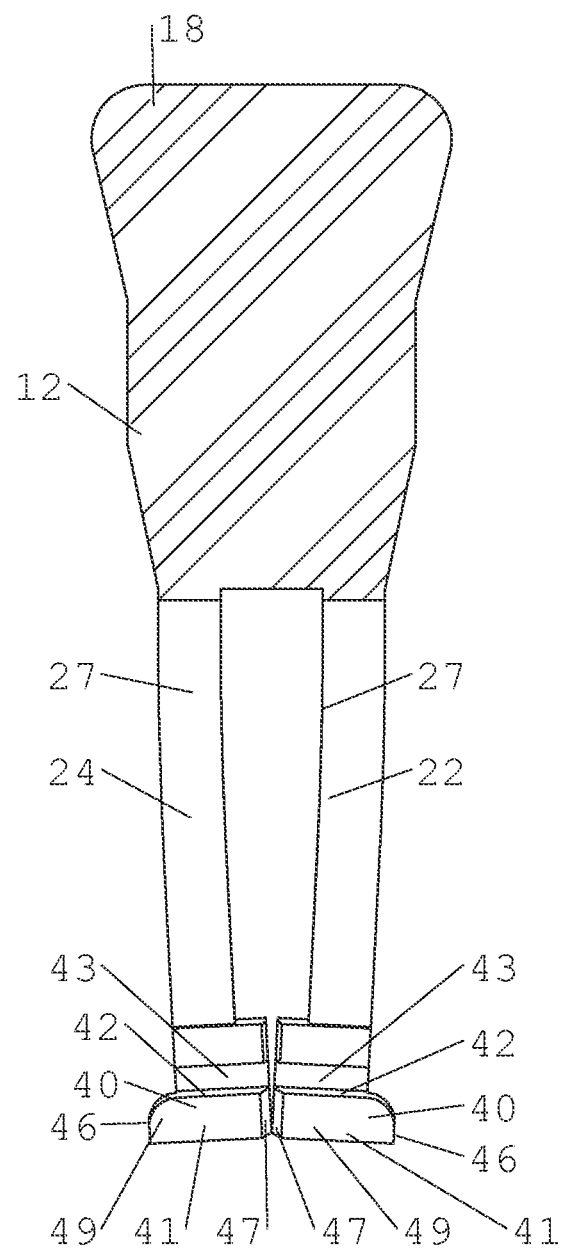
FIG. 5B is a section view taken along line A-A of FIG. 5A illustrating the body of the implant insertion device.
Figure 6A:
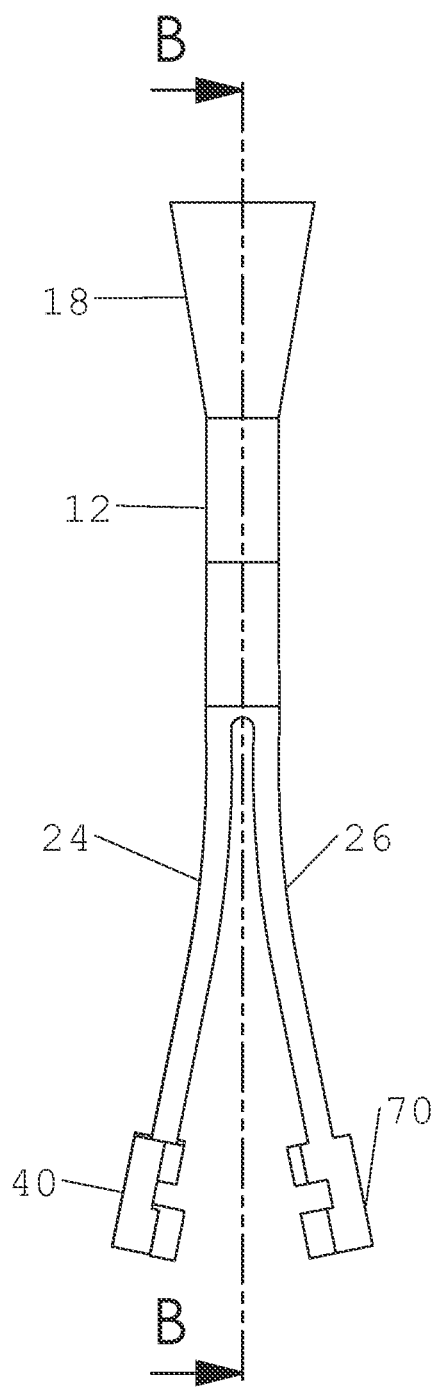
FIG. 6A is a side view illustrating the body of the implant insertion device.
Figure 6B:
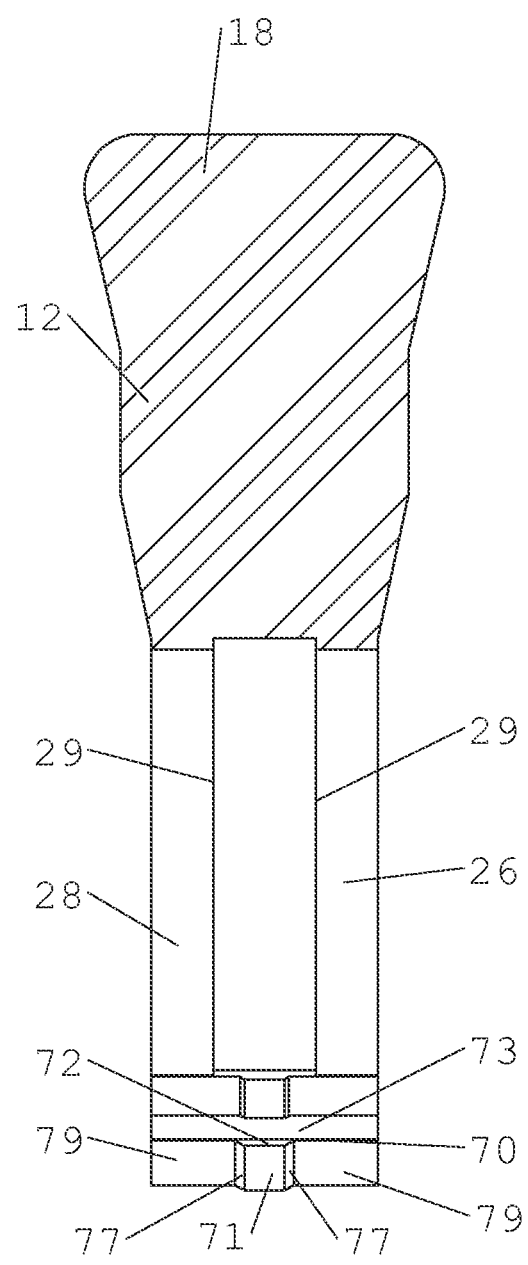
FIG. 6B is a section view taken along line B-B of FIG. 6A illustrating the body of the implant insertion device.
Figure 9:
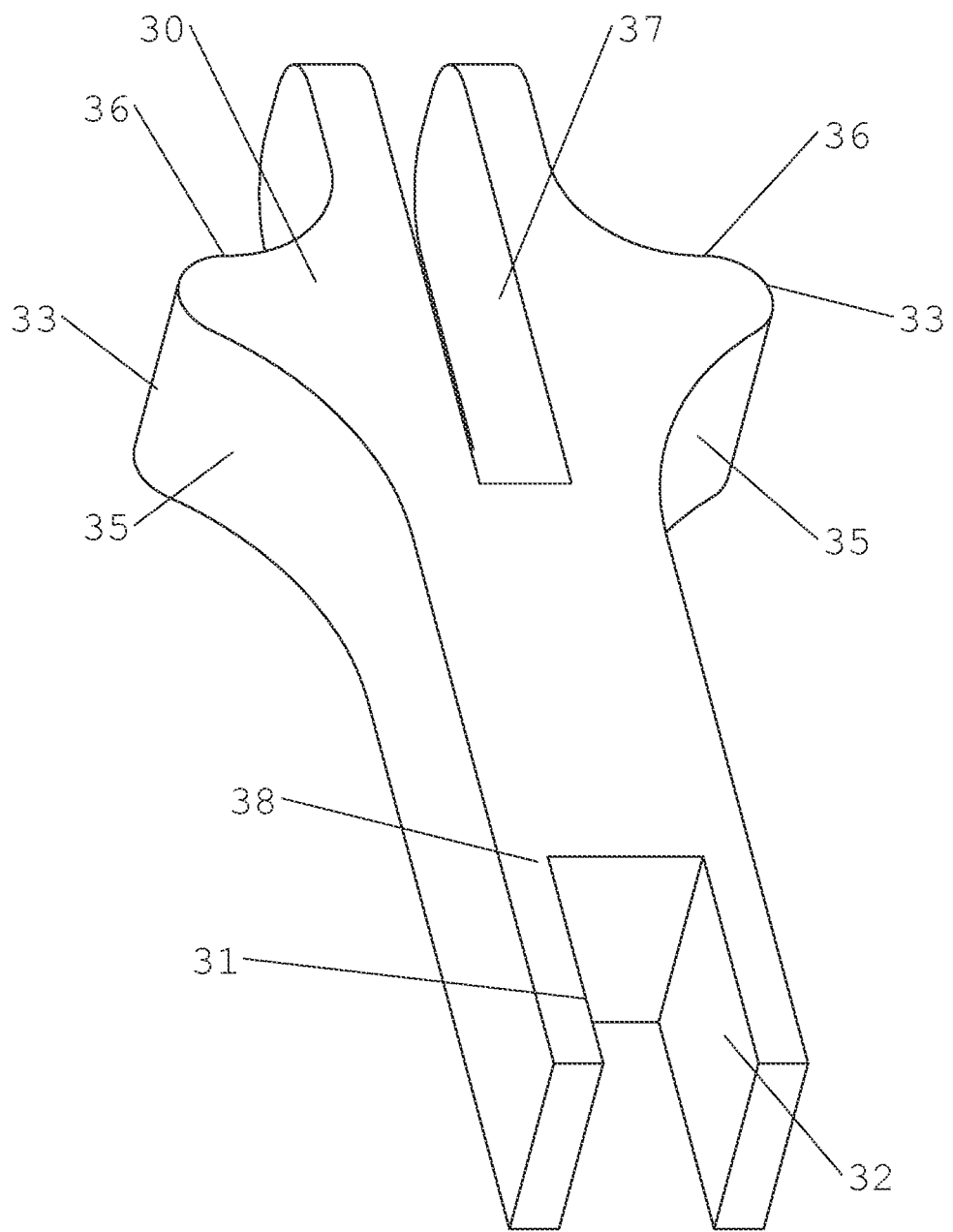
FIG. 9 is a perspective front view illustrating a slider of the implant insertion device.

FIG. 9 illustrates the slider 30. The slider 30 includes a clasp 38 having a clasping surface 31 and a clasping surface 32 that define a slot therebetween. The slider 30 defines a slot 37 and further includes actuators 33 having front faces 35 and back faces 36. The slot 37 allows the slider 30 to secure to the body 12 and to move between its unlocked and locked positions. In particular, placing the slider 30 within the slider guides 27 and 29 and engaging the slider 30 with the slider receiver 8 of the body 12 using the slot 37 secures the slider 30 to the body 12. The actuators 33 allow a user to operate the slider 30 by moving the slider 30 between its unlocked and its locked position. In particular, as shown in FIG. 3, when the back faces 36 of the actuator 33 are pressed, the slider 30 moves within the slider guides 27 and 29 from its unlocked position to its locked position. After reaching the locked position, the user may then press the front face 35 of the actuators 33, which moves the slider 30 within the slider guides 27 and 29 from its locked position to its unlocked position as illustrated in FIG. 2.

The clasp 38 of the slider 30 allows the slider 30 to lock the jaws 40 with the jaw 70. Specifically, when the slider 30 moves from its unlocked position to its locked position, the clasping surfaces 31 and 32 of the clasp 38 engage the slider channels 48 of the jaws 40 and the slider channel 78 of the jaw 70 in a friction fit. The friction fit between the clasping surfaces 31 and 32 and the slider channels 48 and the slider channel 78, respectively, locks the jaws 40 with the jaw 70.

The slider 30, the jaws 40, and the jaw 70 work in concert to load the implant insertion device 10 with the implant 100. The jaws 40 and the jaw 70 begin in their disengaged position as illustrated in FIG. 2 and are moved to their engaged position as illustrated FIG. 3. The jaws 40 and the jaw 70 travel towards each other until the teeth 41 and the tooth 71 mate. Specifically, the tooth interfaces 77 of the tooth 71 engage the tooth interfaces 47 of the teeth 41. Upon engagement, the tooth interfaces 77 of the tooth 71 create a wedging force on the tooth interfaces 47 of the teeth 41. This wedging force moves the jaws 40 and spreads the jaws 40 until the jaw engagement surfaces 49 of the jaws 40 contact the jaw engagement surfaces 79 of the jaw 70 resulting in the mating of the jaws 40 with the jaw 70.

Moving the jaws 40 and the jaw 70 from their disengaged position to their engaged position spreads the arms 22 and 24 and moves the jaws 40 and the arms 22 and 24 downward and horizontally outward. Likewise, the arms 26 and 28 and the jaw 70 move upward such that the jaw 70 moves the jaws 40 to their engaged position whereby the implant 100 is clamped between the jaws 40 and the jaw 70 and secured to the implant insertion device 10.

In an alternative to the first embodiment of the implant insertion device 10, the implant insertion device 10 allows easier removal of the implant 100 from the implant insertion device 10. In particular, the jaws 40 can rotate when moving between the disengaged and the engaged position. Specifically, when the jaws 40 are in the disengaged position, the jaws 40 remain canted downward such that moving the jaws 40 to the engaged position moves the jaws 40 in an upward arc during clamping of the implant 100 by the jaws 40 and the jaw 70. For further clarification, the jaws 40 exhibit a rotation relative to arms 22 and 24 when they are not engaged with the jaw 70. The jaws 40 accordingly travel outward and upward as well as rotate relative to the arms during movement from the disengaged to the engaged position. The rotation of the jaws 40 relative to the arms 22 and 24 helps to insure that the jaws 40 more easily disengage without entanglement from the shape memory implant 100 during the disengagement process.

After the jaws 40 and the jaw 70 move from their disengaged position to their engaged position, the slider 30 moves from its unlocked to its locked position to maintain the jaws 40 and the jaw 70 in their engaged position. In moving from its unlocked to its locked position, the clasp 38 of the slider 30 engages the slider channels 48 of the jaws 40 and the slider channel 78 of the jaw 70 thereby securing the jaws 40 to the jaw 70. Specifically, when the slider 30 moves from its unlocked position to its locked position, the clasping surface 31 engages the slider channels 48 of the jaws 40 in a friction fit and the clasping surface 32 engages the slider channel 78 of the jaw 70 in a friction fit. The friction fit between the clasping surfaces 31 and 32 and the slider channels 48 and slider channel 78, respectively, locks the jaws 40 with the jaw 70. Furthermore, the friction fit between the clasping surface 31 and the slider channels 48 maintains the implant insertion device 10 in its implant engagement position 13 and the jaws 40 and the jaw 70 in their engaged position.

To return the implant insertion device 10 to its implant disengagement position 11, the slider 30 is moved from its locked position to its unlocked position. When the slider 30 moves to its unlocked position, the clasping surface 31 disengages the slider channels 48 of the jaws 40 and the clasping surface 32 disengages the slider channel 78 of the jaw 70 removing the friction fit. Removing the friction fit allows the jaws 40 to be released from the jaw 70 and results in movement of the arms 22 and 24 and the jaws 40 upward and horizontally inward. Likewise, moving the slider 30 from its locked position to its unlocked position allows movement of the arms 26 and 28 and the jaw 70 downward. The movement of the jaws 40 upward and horizontally inward and the jaw 70 downward places the jaws 40 and the jaw 70 in their disengaged position whereby the implant 100 may be released from the implant insertion device 10.

In an alternative embodiment, the slider 30 when moved between its unlocked and locked positions may be configured to move the jaws 40 and the jaw 70 between their disengaged and engaged positions. In particular, the slider 30 may reside within tracks located within the slider guides 27 and 29. Moving the slider 30 from the unlocked position to the locked position moves the slider 30 within the tracks located within the slider guides 27 and 29. The slider 30 applies a force to the slider guide 27 that transfers a force to the arms 22 and 24 and moves the jaws 40 and the arms 22 and 24 downward and horizontally outward. Similarly, the slider 30 applies a force to the slider guide 29 that transfers a force to the arms 26 and 28 and the jaw 70 that moves the jaw 70 upward such that the jaws 40 and the jaw 70 move from their disengaged position to their engaged position whereby the implant 100 is clamped between the jaws 40 and the jaw 70 and secured to the implant insertion device 10.

Moving the slider 30 from the locked position to the unlocked position moves the slider 30 within the tracks located within the slider guides 27 and 29. Moving the slider 30 to the unlocked position releases the force that the slider guide 27 applies to the arms 22 and 24 and moves the jaws 40 and the arms 22 and 24 upward and horizontally inward. Similarly, moving the slider 30 to the unlocked position releases the force that the slider guide 29 applies to the arms 26 and 28 and moves the jaw 70 and the arms 26 and 28 such that the jaws 40 and the jaw 70 move from their engaged position to their disengaged position whereby the implant 100 is released from the implant insertion device 10.

FIGS. 2 and 3 illustrate the operation of securing the implant 100 to the implant insertion device 10 and the removal of the implant 100 from the implant insertion device 10. The implant 100 may be preloaded on the implant insertion device 10 prior to surgery, or the implant 100 may be loaded on the implant insertion device 10 during surgery. The operation of loading the implant 100 on the implant insertion device 10 is as follows.

In a first method to receive the implant 100, the implant insertion device 10 begins in its implant disengagement position 11 wherein the jaws 40 and the jaw 70 reside in their disengaged position. The implant 100 is mechanically deformed from the first final shape 101 into the second shape 102 such that the implant 100 stores mechanical energy. After being mechanically deformed from the first final shape 101 into the second shape 102, the implant 100 is placed over the jaws 40 of the implant insertion device 10 such that a portion of the bridge 120 resides with the bridge channel 43. Specifically, the bottom 122 of the bridge 120 resides adjacent the bridge interfaces 42 and the top 121 of the bridge 120 resides adjacent the arms 22 and 24 of the body 12.

After the implant 100 is placed over the jaws 40, the jaws 40 and the jaw 70 are moved from their disengaged position to their engaged position. In moving from the disengaged position to the engaged position, the jaws 40 move downward and the jaw 70 moves upward. In addition, the tooth interfaces 77 of the tooth 71 engage the tooth interfaces 47 of the teeth 41. Upon engagement, the tooth interfaces 77 of the tooth 71 create a wedging force on the tooth interfaces 47 of the teeth 41 that continues until the jaw engagement surfaces 49 of the jaws 40 contact the jaw engagement surfaces 79 of the jaw 70. This wedging force spreads the arms 22 and 24 and the jaws 40 and moves the arms 22 and 24 and the jaws 40 downward and horizontally outward until the leg interfaces 46 engage the implant 100. Specifically, the leg interfaces 46 engage the implant 100 such that the leg interfaces 46 abut the legs 130 of the implant 100 below the corners 140. Furthermore, moving the jaws 40 and jaw 70 from the disengaged position to the engaged position inserts the bridge 120 of the implant 100 within the bridge channel 73 of the jaw 70. Specifically, the bottom 122 of the bridge 120 resides adjacent the bridge interface 72 and the tops 121 of the bridge 120 resides adjacent the arms 126 and 128 of the body 112 thereby clamping implant 100 between the jaws 40 and the jaw 70. Clamping the implant 100 between the jaws 40 and the jaw 70 maintains the mechanical energy stored in the implant 100 and tensions the implant plant 100 against the jaws 40. In addition, the implant 100 remains loaded on the implant insertion device 10 while jaws 40 maintain the implant 100 in the second shape 102.

After the jaws 40 and the jaw 70 move from the disengaged to the engaged position, the slider 30 is moved from its unlocked to its locked position. In particular, the back faces 36 of the actuators 33 are pressed moving the slider 30 within the slider guides 27 and 29 such that the clasping surfaces 31 and 32 of the clasp 38 engage the slider channels 48 and the slider channel 78, respectively, locking the jaws 40 with the jaw 70.

While the implant 100 may be mechanically deformed from the first final shape 101 into its second shape 102 before placement on the implant insertion device 10, in a second method, the implant 100 also may be placed on the implant insertion device 10 in the first final shape 101 and then mechanically deformed to the second shape 102 by the implant insertion device 10. The jaws 40 and the jaw 70 are moved from their disengaged position to their engaged position using any suitable means such as for example a mechanical press. As described above, moving the jaws 40 and the jaw 70 from their disengage position to their engaged position causes a wedging force that spreads the arms 22 and 24 and the jaws 40 and moves the arms 22 and 24 and the jaws 40 downward and horizontally outward such that the leg interfaces 46 engage the implant 100. This wedging force transfers to the implant 100 such that the implant 100 moves from its first final shape 101 to its second shape 102. This force transfer imparts mechanical energy into the implant 100 and tensions the implant 100 against the jaws 40. Furthermore, the slider 30 moves from its unlocked to its locked position to maintain the jaws 40 and the jaw 70 in the engaged position such that the implant 100 remains loaded on the implant insertion device 10 while the implant insertion device 10 also maintains the implant 100 in the second shape 102. Although not necessary, the implant 100 may be cooled prior to placement on the implant insertion device 10 in order to place it in a martensitic state and aid in movement of the implant 100 from its first final shape 101 to the second shape 102.

After the implant 100 is secured to the implant insertion device 10, the implant 100 is ready to be implanted into tissue or bones. The surgeon places the tips 131 of the implant 100 into predrilled holes or the tips may be impacted into the tissue or bones thereby securing the implant 100 into the tissue or bones. Once the implant 100 is secured to the tissue or bones, it is ready for removal from the implant insertion device 10. To remove the implant 100 from the implant insertion device 10, the surgeon presses the front face 35 of the actuators 33, which moves the slider 30 within the slider guides 27 and 29 from its locked position to its unlocked position. Moving the slider 30 from its locked position to its unlocked position, disengages the clasping surfaces 31 and 32 from the slider channel 48 and the slider channel 78 respectively, thereby allowing the jaws 40 and the jaw 70 to move to the disengaged position.

Moving from the engaged position to the disengaged position allows the jaws 40 to be released from the jaw 70 allowing upward movement of the jaws 40 and downward movement of the jaw 70. Furthermore, the arms 22 and 24 and the jaws 40 move upward and horizontally inward and the arms 26 and 28 and the jaw 70 move downward such that the implant 100 may be released from the implant insertion device 10. When the jaws 40 and the jaw 70 are in their disengaged position, the leg interfaces 46 of the jaws 40 no longer abut the legs 130 of the implant 100, resulting in the release of the tension between the implant 100 and the jaws 40 and a release of the implant 100 from the implant insertion device 10.

In the event the implant 100 remains engaged with the jaws 40 after the jaws 40 and the jaw 70 have moved from their engaged position to the disengaged position, the implant 100 may be removed from the implant insertion device 10 by applying a twisting force. In particular, if the implant 100 remains engaged with either the bridge channel 43 of the jaws 40 or the bridge channel 73 of the jaw 70, applying a twisting force to the implant insertion device 10 removes the implant 100 therefrom. The twisting or rotational force overcomes the force the bridge channel 43 or the bridge channel 73 applies against the implant 100. As a result, the bridge channel 43 or the bridge channel 73 separates from the implant 100, thereby releasing the implant 100 from the implant insertion device 10.

After the implant 100 is removed from the implant insertion device 10, the implant 100 is tamped down to fully engage the tissue or bone. Once fully engaged, the implant 100 moves from its second shape 102 to its first final shape 101, thereby releasing its mechanical energy into the tissue or bone. As the implant 100 moves from its second shape 102 to its first final shape 101, the implant 100 places a constant force on the tissue or bones that fuses the tissue or bone together and aids the healing process.

The design of the implant insertion device 10 allows a gradual release of the implant 10. In particular, if the surgeon presses actuators 33 quickly, then the slider 30 moves from its locked to its unlocked position quickly and the jaws 40 and the jaw 70 move from their engaged position to their disengaged position quickly thereby rapidly releasing the implant 100. On the other hand, if the surgeon believes a patient has poor bone quality, the surgeon can slowly press the actuators 33, which slowly moves the slider 30 from the locked to the unlocked position. Slowly moving the slider 30 from the locked to the unlocked position allows the jaws 40 and the jaw 70 to slowly move from their engaged position to their disengaged position thereby gradually releasing the implant 100.

FIGS. 10A-12 illustrate a second embodiment of an implant insertion device 500 and an implant 200. The implant 200 is secured to the implant insertion device 500 allowing a surgeon to insert the implant 200 into tissue or bone during surgery.

In the second embodiment, the implant 200 is a surgical staple and includes two bridges 210 and 211 and legs 220 formed integrally at corners 230. The bridges 210 and 211 each include a top 212, a bottom 213, a back 214, and a front 215. The legs 220 further include tips 221 which may form a shape that is rounded for insertion into drill holes or the tips 221 may be pointed for impaction into bones. While the second embodiment discloses the implant 200 as a surgical staple, it should be understood by one of ordinary skill in the art that any implant adapted to engage and span bone such that the implant exerts a force, typically a compressive force, to the bone is suitable for the present invention.

Figure 10A:
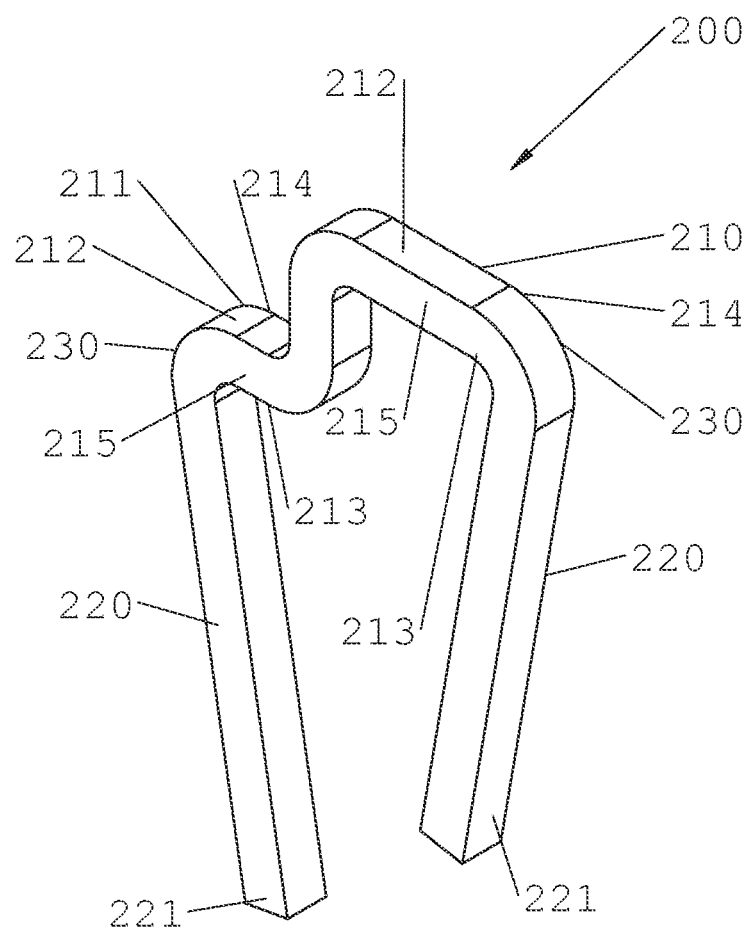
FIG. 10A is a perspective view of an implant a first shape for use with an implant insertion device according to a second embodiment.
Figure 10B:
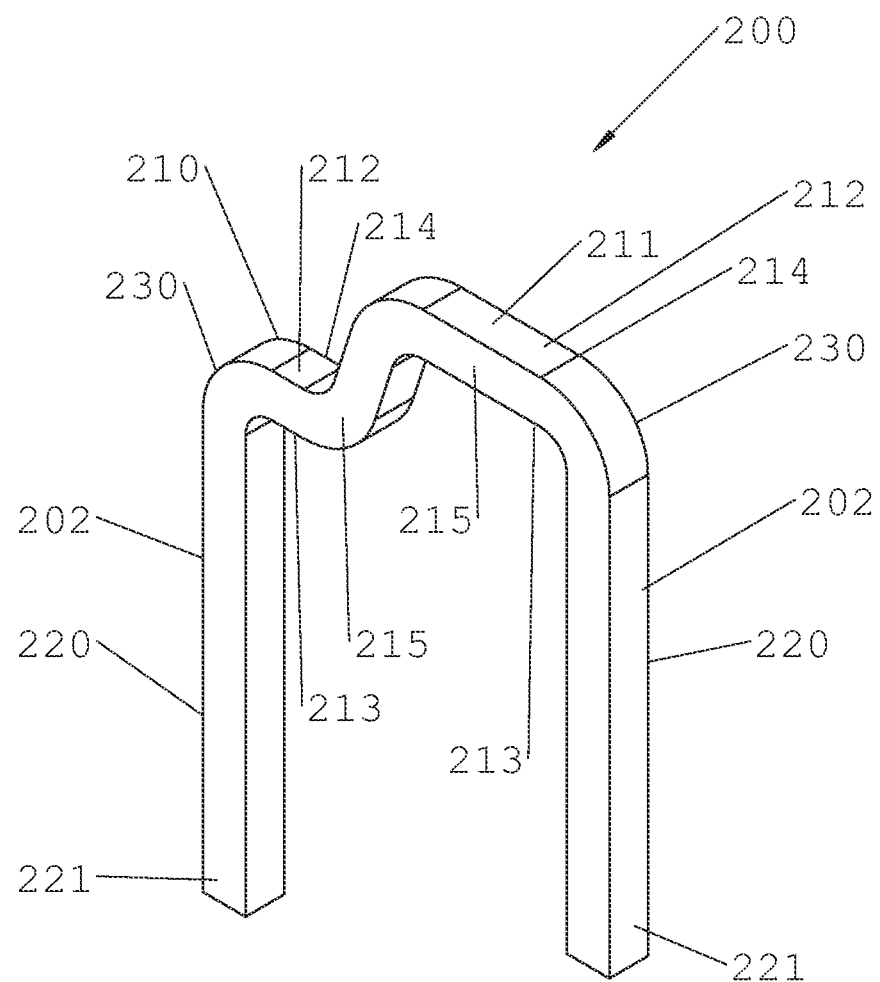
FIG. 10B is a perspective view of the implant in a second shape for use with the implant insertion device according to the second embodiment.

The implant 200 is composed of a shape memory material such as Nitinol that allows the implant 200 to have a first shape 201 as illustrated in FIG. 10A and the ability to transform into a second shape 202 as illustrated in FIG. 10B. The shape memory material gives the implant 200 elastic properties in that the implant 200 stores mechanical energy and is subject to elastic (recoverable) deformation when it releases the stored mechanical energy. The implant 200 is mechanically deformed into the second shape 202 and held in the second shape 202 by the implant insertion device 500 such that, upon release from the implant insertion device 500, the implant 200 elastically deforms from the second shape 202 into the first shape 201.

The implant insertion device 500 includes a body 112 and a slider 130 that moves between an unlocked and a locked position. The implant insertion device 500 exists in either an implant disengagement position 111 (shown in FIG. 11) or an implant engagement position 113 (shown in FIG. 12) and is movable therebetween. In the implant disengagement position 111, the implant 200 slips in or out of position in the implant insertion device 500 with no obstruction. In the implant engagement position 113, the implant insertion device 500 engages the implant 200 and maintains the implant 200 in the second shape 202. In addition, the implant insertion device 500 allows a surgeon to manipulate the implant 200 and insert the implant 200 into tissue or bones that require fixating. The implant insertion device 500 can be made of any suitable material; however, in the first embodiment the implant insertion device 500 is made from plastic.

Figure 13:
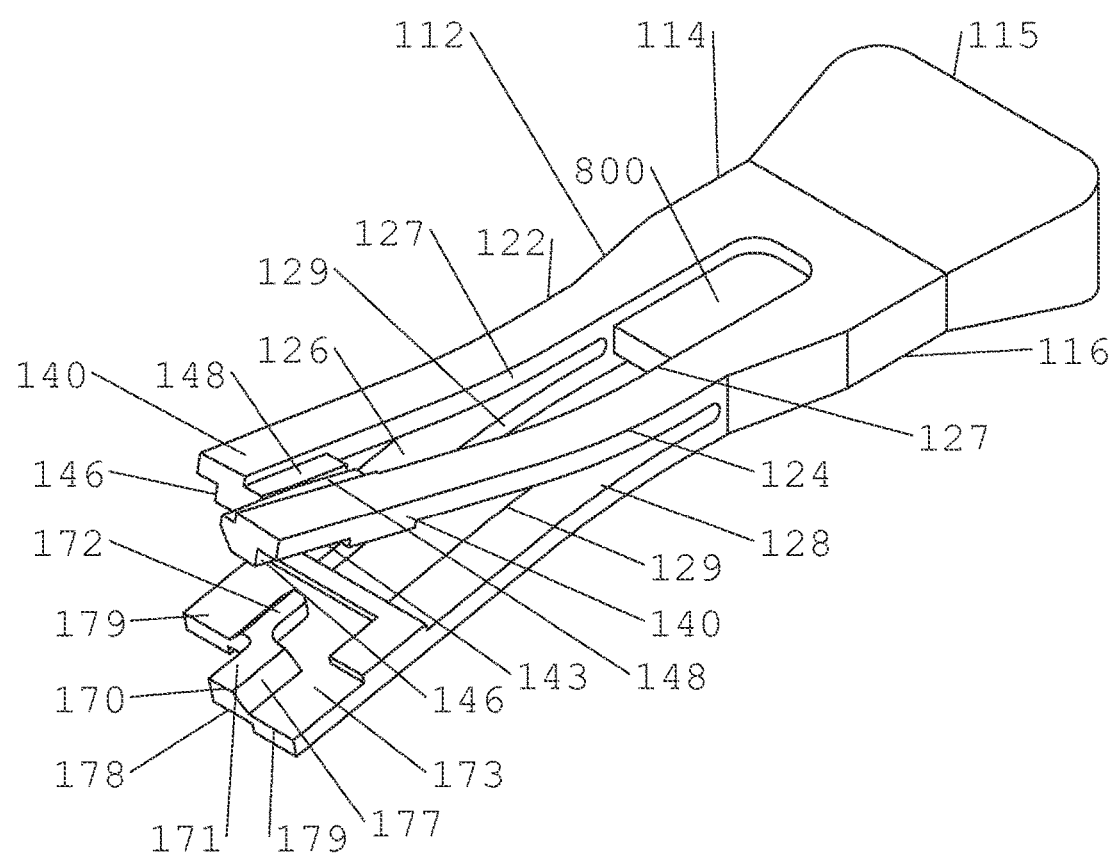
FIG. 13 is a perspective front view illustrating a body of the implant insertion device.
Figures 14A, 14B:
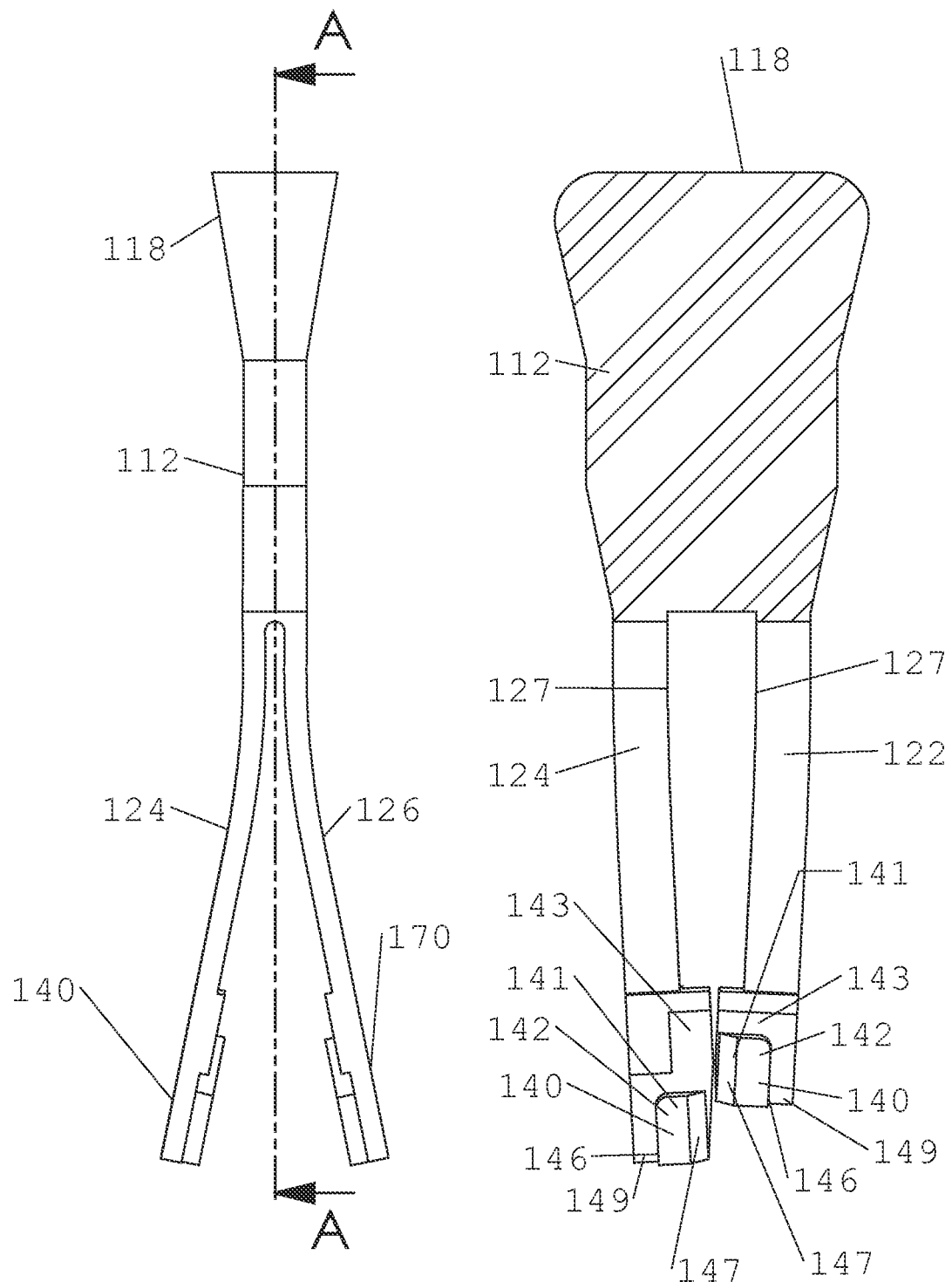
FIG. 14A is a side view illustrating the body of the implant insertion device.
FIG. 14B is a section view taken along line A-A of FIG. 14A illustrating the body of the implant insertion device.
Figure 15A:
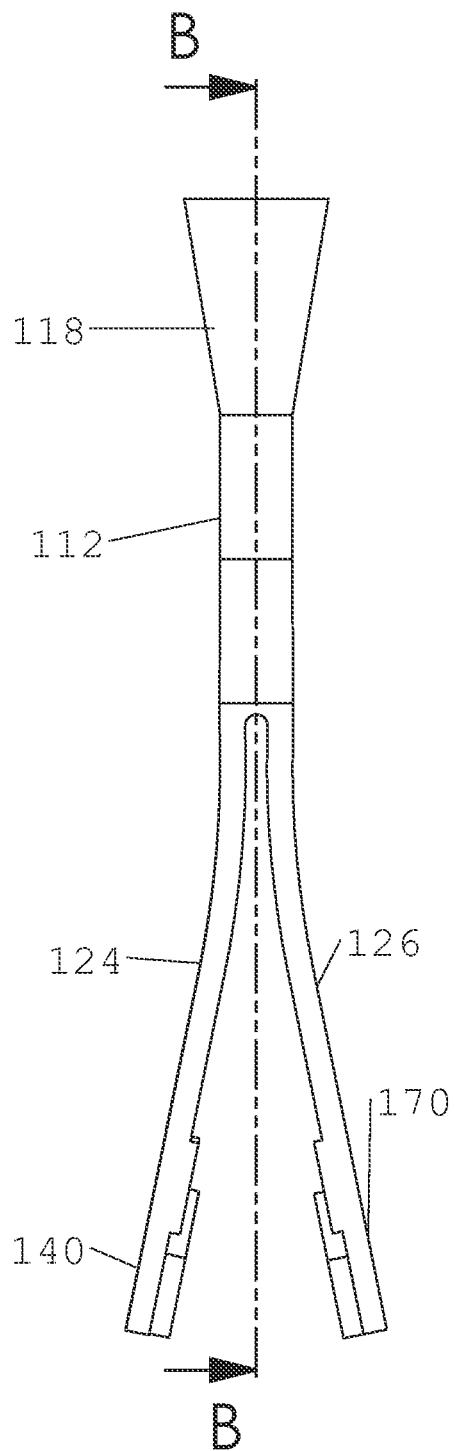
FIG. 15A is a side view illustrating the body of the implant insertion device.
Figure 15B:
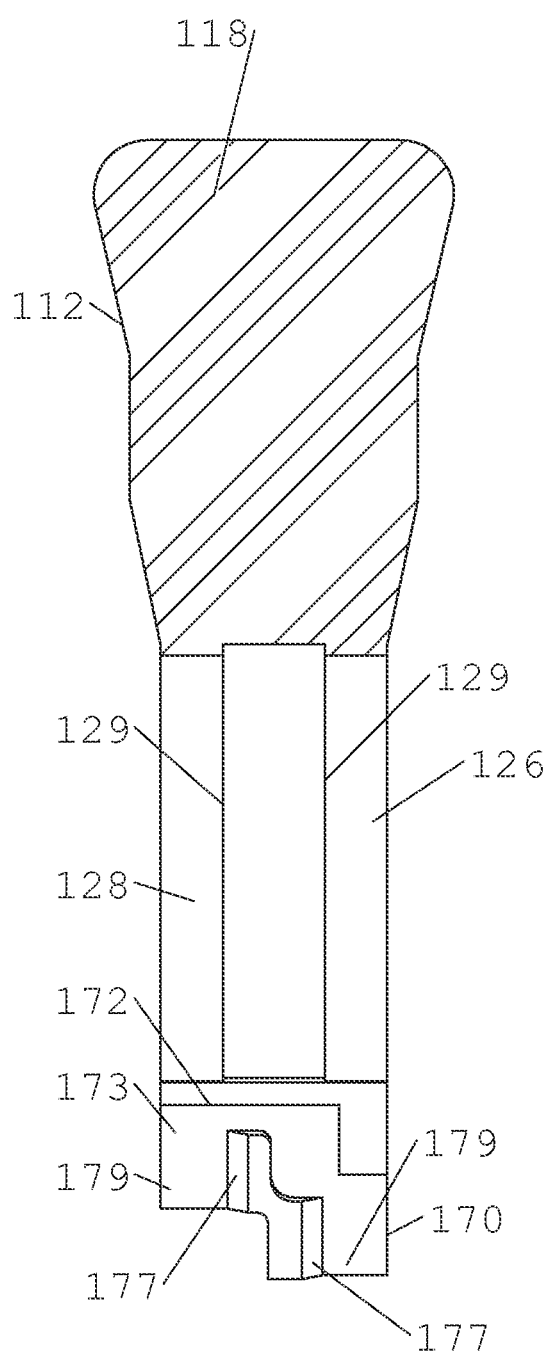
FIG. 15B is a section view taken along line B-B of FIG. 15A illustrating the body of the implant insertion device.

FIGS. 13-15B illustrate the body 112 of the implant insertion device 500. The body 112 of the implant insertion device 500 includes a slider receiver 800, a front 114, a back 116, a handle 118 having a top 115, arms 122 and 124, and arms 126 and 128. The slider receiver 800 is defined by flat grooves in the body 112 that receive a portion of the slider 130 to allow the securing of the slider 130 over the slider receiver 800 and thus to the body 112. The handle 118 provides a gripping surface on the front 114 and the back 116 of the body 112. The gripping surface of the handle 118 allows a surgeon to manipulate the implant insertion device 500 and therefore the implant 200 that is secured thereto. The arms 122 and 124 and the arms 126 and 128 attach to the handle 118 and include jaws 140 and a jaw 170, respectively. The jaws 140 and the jaw 170 move between a disengaged position and an engaged position. Furthermore, the arms 122 and 124 and the arms 126 and 128 form slider guides 127 and 129 respectively. The slider guides 127 and 129 allow the slider 130 to move between its unlocked and locked position. As shown in FIG. 13, the arms 122 and 126 are shorter in length than the arms 124 and 128 to accommodate the difference in bridge height of the staple implant 200. The arms 122 and 124 and the arms 126 and 128 are designed to be flexible if an external force is applied thereto. One of ordinary skill in the art will recognize that the arms 122 and 124 and the arms 126 and 128 can be at many relative angles from each other. One skilled in the art will further recognize that the length and height difference of the arms 122 and 124 and the arms 126 and 128 may vary to deliver a variety of results.

In the preferred embodiment, the body 112 of the implant insertion device 500 is manufactured in one piece using a mold. However, the body 112 of the implant insertion device 50 could be manufactured in two separate pieces. In particular, the arms 122 and 124, the jaws 140, and a portion of the handle 118 form the first piece and the arms 126 and 128, the jaw 170, and a portion of the handle 118 form the second piece. These two pieces are fastened together using any suitable means such as a hinge or an adhesive to create the body 112.

The jaws 140 include teeth 141 that engage the implant 200 and the jaw 170 and slider channels 148 that engage the slider 130 as the slider 130 moves between its unlocked and its locked position. The teeth 141 include bridge interfaces 142 and leg interfaces 146 that engage the bridges 210 and 211 of the implant 200 as well as tooth interfaces 147 and jaw interfaces 149 that engage the jaw 170. Specifically, the bridge interfaces 142 and a portion of the arms 122 and 124 form a bridge channel 143 that receives a portion of the bridges 210 and 211 therein. Furthermore, the leg interfaces 146 engage the implant 200 such that the leg interfaces 146 abut the legs 230 of the implant 200 below the corners 240. The tooth interfaces 147 engage a portion of the jaw 170 that moves the jaws 140 from the disengaged position to the engaged position and aid in securing the implant 200 to the implant insertion device 500.

The jaw 170 includes a tooth 171 that engages the implant 200 and the jaws 140 and a slider channel 178 that engages the slider 130 as the slider 130 moves between its unlocked and its locked position. The tooth 171 includes a bridge interface 172 that engages the bridges 210 and 211 of the implant 200 and tooth interfaces 177 and jaw interfaces 179 that engage the jaws 140. The bridge interface 172 and a portion of the arms 126 and 128 form a bridge channel 173 that receives a portion of the bridges 210 and 211 therein.

Figure 16:
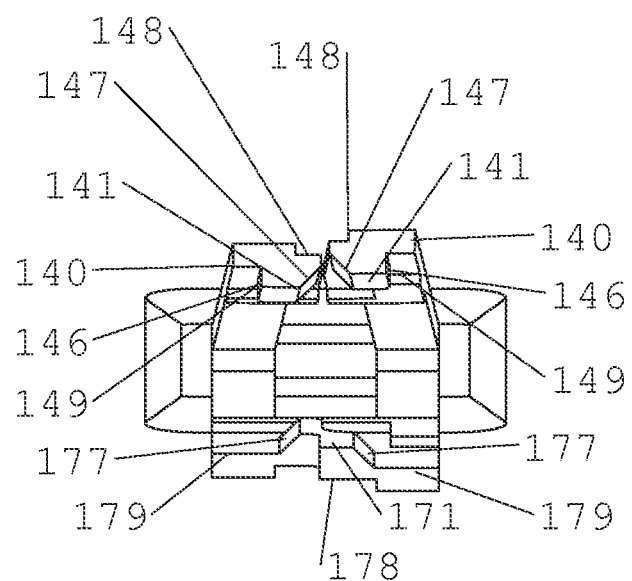
FIG. 16 is a front view illustrating the implant insertion device in the implant disengagement position.
Figure 17:
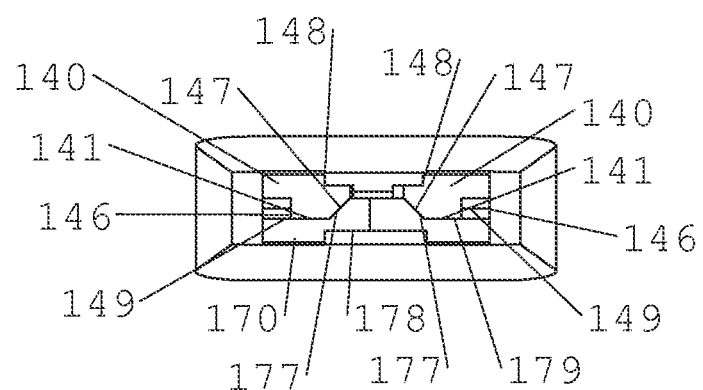
FIG. 17 is a front view illustrating the implant insertion device in the implant engagement position.

The jaws 140 and the jaw 170 move between the disengaged position and the engaged position to aid in the securing and removal of the implant 200. Specifically, as the implant insertion device 500 moves from its implant disengagement position 111 to its implant engagement position 113, the jaws 140 and the jaw 170 move from their disengaged position to their engaged position whereby the tooth interfaces 177 of the jaw 170 engage the tooth interfaces 147 of the jaw 140. As illustrated in FIGS. 16 and 17, the tooth interfaces 147 of the jaws 140 as well as the tooth interfaces 177 of the jaw 170 are beveled in order to aid in the securing and the removal of the implant 200 from the implant insertion device 500. In the first embodiment, the beveling of the tooth interfaces 147 of the jaws 140 and the tooth interfaces 177 of the jaw 170 reduces the normal force between contacting surfaces and thus the friction force between the jaws 140 and the jaw 170 as the implant insertion device 500 moves between its implant disengagement position 111 and its implant engagement position 113. The beveling of the of the tooth interfaces 147 of the jaws 140 and tooth interfaces 177 of the jaw 170 also creates a ramp that allows the jaw 170 to force open the jaws 140 similar to a wedge when the implant insertion device 500 moves from its disengagement position 111 to its implant engagement position 113. One of ordinary skill in the art will recognize that the angle of the bevel and application of trigonometry determines the friction force between the tooth interfaces 147 of the jaws 140 and the tooth interfaces 177 of the jaw 170. Reducing the amount of friction force between the tooth interfaces 147 of the jaws 140 and the tooth interfaces 177 of the jaw 170 aids in removing the implant 200 from the implant insertion device 500. Furthermore, the angle of the bevel also determines the force for separating the jaws 140 when the implant insertion device 200 moves from its implant disengagement position 111 to its implant engagement position 113.

Figure 11:
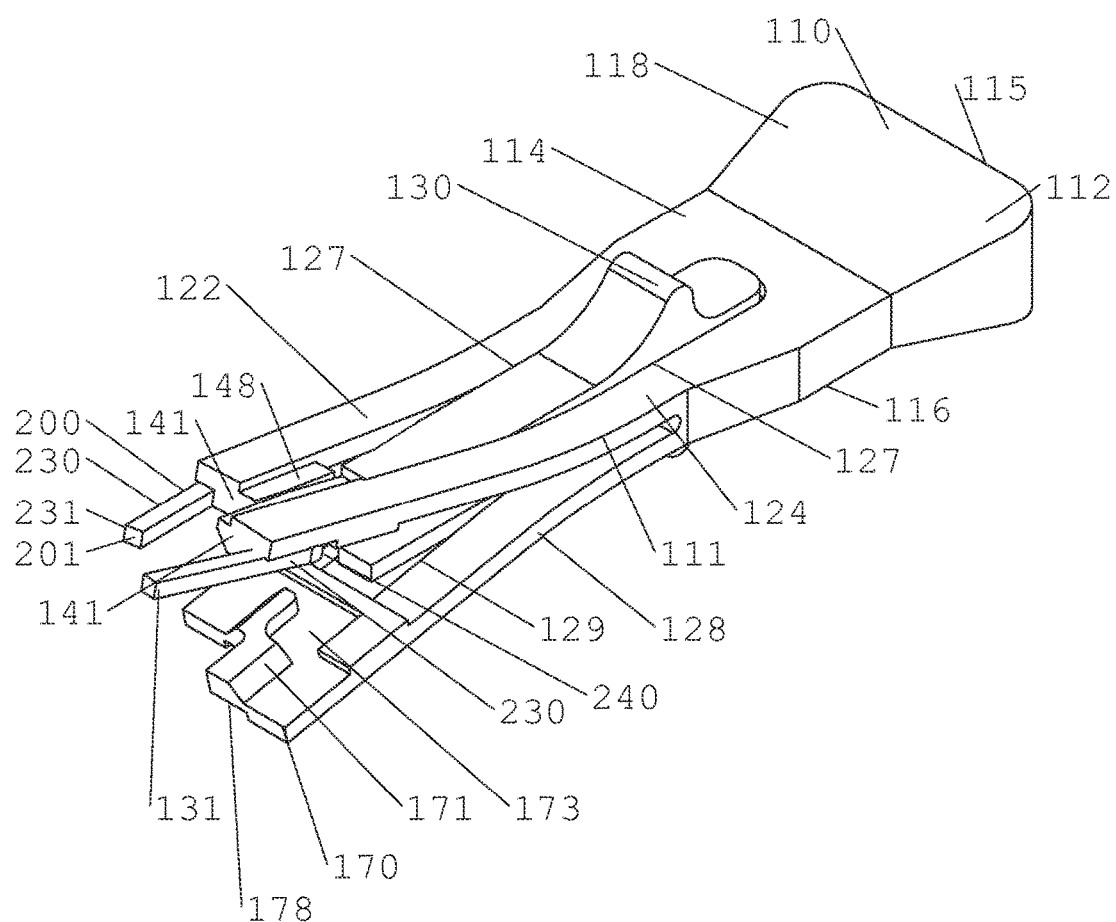
FIG. 11 is a perspective front view illustrating the implant and the implant insertion device in an implant disengagement position.
Figure 12:
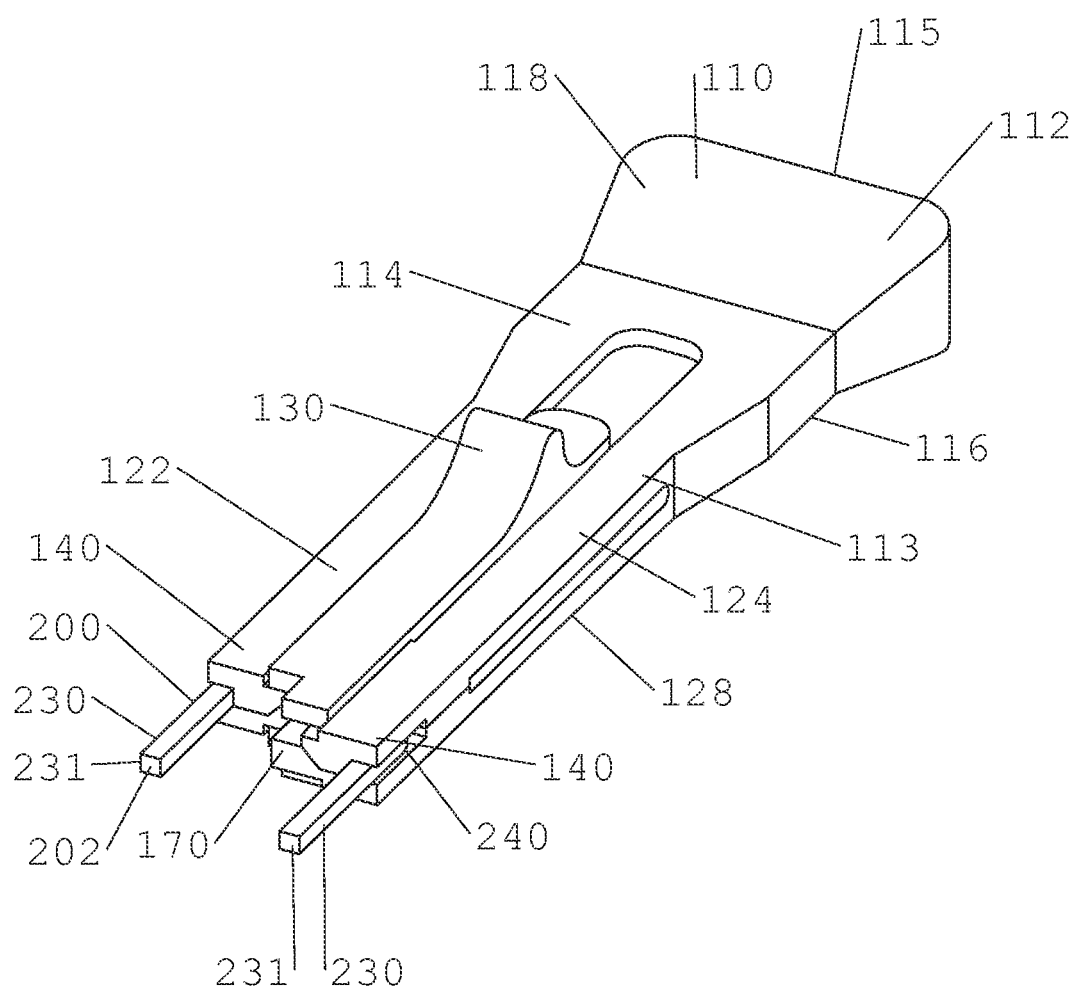
FIG. 12 is a perspective front view illustrating the implant and the implant insertion device in an implant engagement position.
Figure 18:
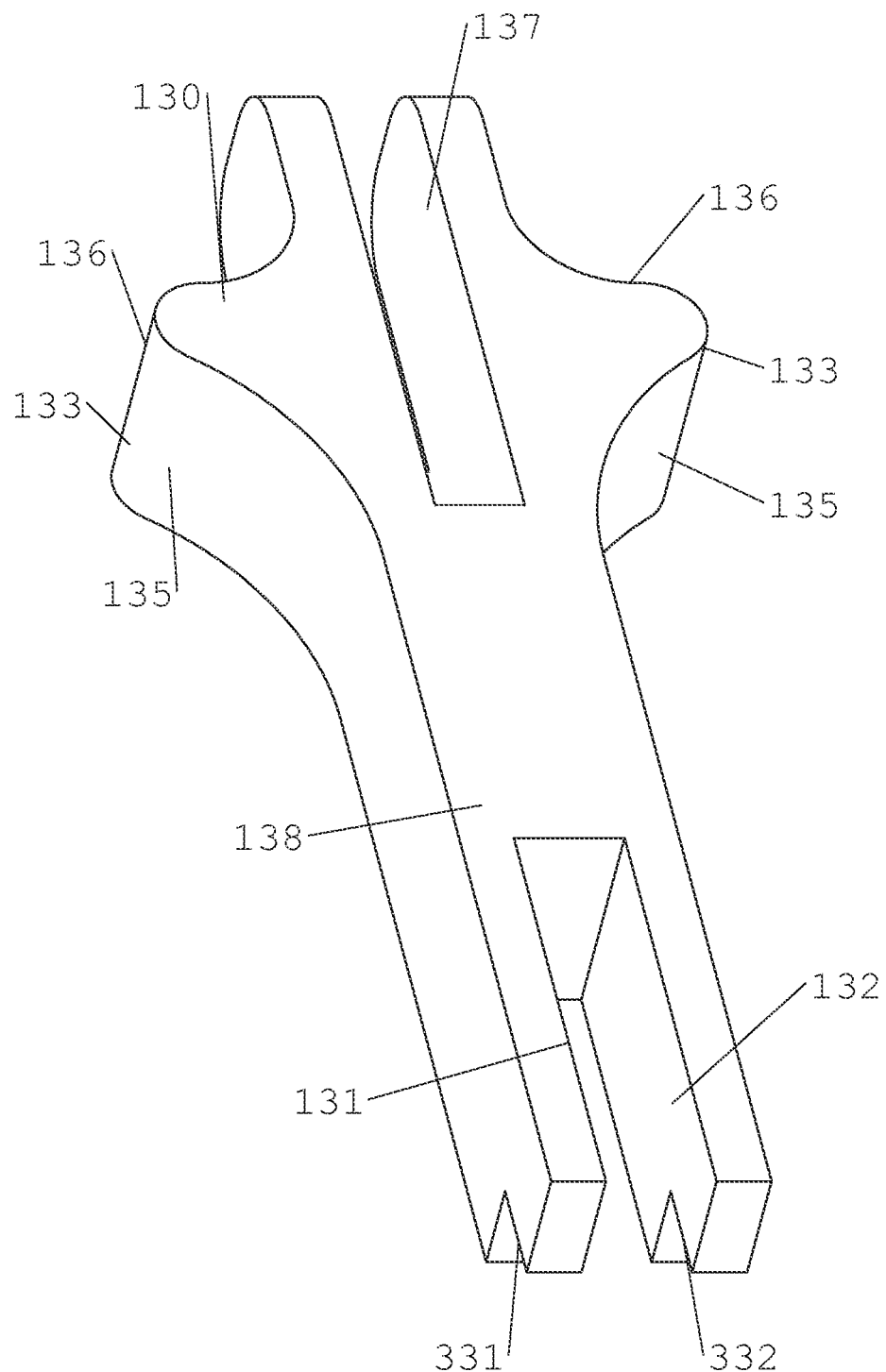
FIG. 18 is a perspective front view illustrating a slider of the implant insertion device.

FIG. 18 illustrates the slider 130. The slider 130 includes a clasp 138 having a clasping surface 131 and a clasping surface 132 that define a slot therebetween. The clasp 138 includes notches 331 and 332 to accommodate the difference in lengths between the arms 122 and 126 and the arms 124 and 128. The slider 130 defines a slot 137 and further includes actuators 133 having front faces 135 and back faces 136. The slot 137 allows the slider 130 to secure to the body 112 and to move between its unlocked and its locked position. In particular, placing the slider 130 within the slider guides 127 and 129 and engaging the slider 130 with the slider receiver 800 of the body 112 using the slot 137 secures the slider 130 to the body 112. The actuators 133 allow a user to operate the slider 130 by moving the slider 130 between its unlocked and its locked position. In particular, as shown in FIG. 12, when the back faces 136 of the actuator 133 are pressed, the slider 130 moves within the slider guides 127 and 129 from its unlocked position to its locked position. After reaching the locked position, the user may then press the front face 135 of the actuators 133, which moves the slider 130 within the slider guides 127 and 129 from its locked position to its unlocked position as illustrated in FIG. 11.

The clasp 138 of the slider 130 allows the slider 130 to lock the jaws 140 with the jaw 170. Specifically, when the slider 130 moves from its unlocked position to its locked position, the clasping surfaces 131 and 132 of the clasp 1138 engage the slider channels 148 of the jaws 140 and the slider channel 178 of the jaw 170 in a friction fit. The friction fit between the clasping surfaces 131 and 132 and the slider channels 148 and the slider channel 178, respectively, locks the jaws 140 with the jaw 170.

The slider 130, the jaws 140, and the jaw 170 work in concert to load the implant insertion device 500 with the implant 200. The jaws 140 and the jaw 170 begin in their disengaged position as illustrated in FIG. 11 and are moved to their engaged position as illustrated FIG. 12. The jaws 140 and the jaw 170 travel towards each other until the teeth 141 and the tooth 171 mate. Specifically, the tooth interfaces 177 of the tooth 171 engage the tooth interfaces 147 of the teeth 141. Upon engagement, the tooth interfaces 177 of the tooth 171 create a wedging force on the tooth interfaces 147 of the teeth 141. This wedging force moves the jaws 140 and spreads the jaws 140 until the jaw engagement surfaces 149 of the jaws 140 contact the jaw engagement surfaces 179 of the jaw 170 resulting in the mating of the jaws 140 with the jaw 170.

Moving the jaws 140 and the jaw 170 from their disengaged position to their engaged position spreads the arms 122 and 124 and moves the jaws 140 and the arms 122 and 124 downward and horizontally outward. Likewise, the arms 126 and 128 and the jaw 170 move upward such that the jaw 170 moves the jaws 140 to their engaged position whereby the implant 200 is clamped between the jaws 140 and the jaw 170 and secured to the implant insertion device 500.

In an alternative to the second embodiment of the implant insertion device 500, the implant insertion device 500 allows easier removal of the implant 200 from the implant insertion device 500. In particular, the jaws 140 can rotate when moving between the disengaged position and the engaged position. Specifically, when the jaws 140 are in the disengaged position, the jaws 140 remain canted downward such that moving the jaws 140 to the engaged position moves the jaws 140 in an upward arc during clamping of the implant 200 by the jaws 140 and the jaw 170. For further clarification, the jaws 140 exhibit a rotation relative to arms 122 and 124 when they are not engaged with the jaw 170. The jaws 140 accordingly travel outward and upward as well as rotate relative to the arms during movement from the disengaged position to the engaged position. The rotation of the jaws 140 relative to the arms 122 and 124 helps to insure that the jaws 140 more easily disengage without entanglement from the shape memory implant 200 during the disengagement process.

After the jaws 140 and the jaw 170 prove from their disengaged position to their engaged position, the slider 130 troves from its unlocked to its locked position to maintain the jaws 140 and the jaw 170 in their engaged position. In moving from its unlocked to its locked position, the clasp 138 of the slider 130 engages the slider channels 148 of the jaws 140 and the slider channel 178 of the jaw 170 thereby securing the jaws 140 to the jaw 170. Specifically, when the slider 130 moves from s unlocked position to its locked position, the clasping surface 131 engages the slider channels 148 of the jaws 140 in a friction fit and the clasping surface 132 engages the slider channel 178 of the jaw 170 in a friction fit. The friction fit between the clasping surfaces 131 and 132 and the slider channels 148 and slider channel 178 respectively, locks the jaws 140 with the jaw 170. Furthermore, the friction fit between the clasping surface 131 and the slider channels 148 maintains the implant insertion device 500 in its implant engagement position 113 and the jaws 140 and the jaw 170 in their engaged position.

To return the implant insertion device 500 to its implant disengagement position 111, the slider 130 is moved from its locked position to its unlocked position. When the slider 130 moves to its unlocked position, the clasping surface 131 disengages the slider channels 148 of the jaws 140 and the clasping surface 132 disengages the slider channel 178 of the jaw 170 removing the friction fit. Removing the friction fit allows the jaws 140 to be released from the jaw 170 and results in movement of the arms 122 and 124 and the jaws 140 upward and horizontally inward. Likewise, moving the slider 130 from its locked position to its unlocked position allows movement of the arms 126 and 128 and the jaw 170 downward. The movement of the jaws 140 upward and horizontally inward and the jaw 170 downward places the jaws 140 and the jaw 170 in their disengaged position whereby the implant 200 may be released from the implant insertion device 500.

In an alternative embodiment, the slider 130 when moved between its unlocked and locked positions may be configured to move the jaws 140 and the jaw 170 between their disengaged and engaged positions. In particular, the slider 30 may reside within tracks located within the slider guides 127 and 129. Moving the slider 130 from the unlocked position to the locked position moves the slider 130 within the tracks located within the slider guides 127 and 129. The slider 130 applies a force to the slider guide 127 that transfers a force to the arms 122 and 124 and moves the jaws 140 and the arms 122 and 124 downward and horizontally outward. Similarly, the slider 130 applies a force to the slider guide 129 that transfers a force to the arms 126 and 128 and the jaw 170 that moves the jaw 170 upward such that the jaws 140 and the jaw 170 move from their disengaged position to their engaged position whereby the implant 200 is clamped between the jaws 140 and the jaw 170 and secured to the implant insertion device 500.

Moving the slider 130 from the locked position to the unlocked position moves the slider 130 within the tracks located within the slider guides 127 and 129. Moving the slider 130 to the unlocked position releases the force that the slider guide 127 applies to the arms 122 and 124 and moves the jaws 140 and the arms 122 and 124 upward and horizontally inward. Similarly, moving the slider 130 to the unlocked position releases the force that the slider guide 129 applies to the arms 126 and 128 and moves the jaw 170 and the arms 126 and 128 such that the jaws 140 and the jaw 170 move from their engaged position to their disengaged position whereby the implant 200 is released from the implant insertion device 500.

FIGS. 11 and 12 illustrate the operation of securing the implant 200 to the implant insertion device 500 and the removal of the implant 200 from the implant insertion device 500. The implant 200 may be preloaded on the implant insertion device 500 prior to surgery, or the implant 200 may be loaded on the implant insertion device 500 during surgery. The operation of loading the implant 200 on the implant insertion device 500 is as follows.

In a first method to receive the implant 200, the implant insertion device 500 begins in its implant disengagement position 111 wherein the jaws 140 and the jaw 170 reside in their disengaged position. The implant 200 is mechanically deformed from the first final shape 201 into the second shape 202 such that the implant 200 stores mechanical energy. After being mechanically deformed from the first final shape 201 into the second shape 202, the implant 200 is placed over the jaws 140 of the implant insertion device 500 such that a portion of the bridges 210 and 211 reside with the bridge channel 143. Specifically, the bottoms 123 of the bridges 210 and 211 reside adjacent the bridge interfaces 142 and the tops 212 of the bridges 210 and 211 reside adjacent the arms 122 and 124 of the body 112.

After the implant 200 is placed over the jaws 140, the jaws 140 and the jaw 170 are moved from their disengaged position to their engaged position. In moving from the disengaged position to the engaged position, the jaws 140 move downward and the jaw 170 moves upward. In addition, the tooth interfaces 177 of the tooth 171 engage the tooth interfaces 147 of the teeth 141. Upon engagement, the tooth interfaces 177 of the tooth 171 create a wedging force on the tooth interfaces 147 of the teeth 141 that continues until the jaw engagement surfaces 149 of the jaws 140 contact the jaw engagement surfaces 179 of the jaw 170. This wedging force spreads the arms 122 and 124 and the jaws 140 and moves the arms 122 and 124 and the jaws 140 downward and horizontally outward until the leg interfaces 146 engage the implant 200. Specifically, the leg interfaces 146 engage the implant 200 such that the leg interfaces 146 abut the legs 230 of the implant 200 below the corners 240. Furthermore, moving the jaws 140 and jaw 170 from the disengaged position to the engaged position inserts the bridges 210 and 211 of the implant 200 within the bridge channel 173 of the jaw 170. Specifically, the bottoms 123 of the bridges 210 and 211 reside adjacent the bridge interface 172 and the tops 212 of the bridges 210 and 211 reside adjacent the arms 126 and 128 of the body 112 thereby clamping implant 200 between the jaws 140 and the jaw 170. Clamping the implant 200 between the jaws 140 and the jaw 170 maintains the mechanical energy stored in the implant 200 and tensions the implant plant 200 against the jaws 140. In addition, the implant 200 remains loaded on the implant insertion device 500 while jaws 140 maintain the implant 200 in the second shape 202.

After the jaws 140 and the jaw 170 move from the disengaged to the engaged position, the slider 130 is moved from its unlocked to its locked position. In particular, the back faces 136 of the actuators 133 are pressed moving the slider 130 within the slider guides 127 and 129 such that the clasping surfaces 131 and 132 of the clasp 138 engage the slider channels 148 and the slider channel 178, respectively, locking the jaws 140 with the jaw 170.

While the implant 200 may be mechanically deformed from the first final shape 201 into its second shape 202 before placement on the implant insertion device 500, in a second method, the implant 200 also may be placed on the implant insertion device 500 in the first final shape 201 and then mechanically deformed to the second shape 202 by the implant insertion device 500. The jaws 140 and the jaw 170 are moved from their disengaged position to their engaged position using any suitable means such as for example a mechanical press. As described above, moving the jaws 140 and the jaw 170 from their disengage position to their engaged position causes a wedging force that spreads the arms 122 and 124 and the jaws 140 and moves the arms 122 and 124 and the jaws 140 downward and horizontally outward such that the leg interfaces 146 engage the implant 200. This wedging force transfers to the implant 200 such that the implant 200 moves from its first final shape 201 to its second shape 202. This force transfer imparts mechanical energy into the implant 200 and tensions the implant 200 against the jaws 140. Furthermore, the slider 130 moves from its unlocked to its locked position to maintain the jaws 140 and the jaw 170 in the engaged position such that the implant 200 remains loaded on the implant insertion device 500 while the implant insertion device 500 also maintains the implant 200 in the second shape 202. Although not necessary, the implant 200 may be cooled prior to placement on the implant insertion device 500 in order to place it in a martensitic state and aid in movement of the implant 200 from its first final shape 201 to the second shape 202.

After the implant 200 is secured to the implant insertion device 500, the implant 200 is ready to be implanted into tissue or bones. The surgeon places the tips 231 of the implant 200 into predrilled holes or the tips may be impacted into the tissue or bones thereby securing the implant 200 into the tissue or bones. Once the implant 200 is secured to the tissue or bones, it is ready for removal from the implant insertion device 500. To remove the implant 200 from the implant insertion device 500, the surgeon presses the front face 135 of the actuators 133, which moves the slider 130 within the slider guides 127 and 129 from its locked position to its unlocked position. Moving the slider 130 from its locked position to its unlocked position, disengages the clasping surfaces 131 and 132 from the slider channel 148 and the slider channel 178 respectively, thereby allowing the jaws 140 and the jaw 170 to move to the disengaged position.

Moving from the engaged position to the disengaged position allows the jaws 140 to be released from the jaw 170 allowing upward movement of the jaws 140 and downward movement of the jaw 170. Furthermore, the arms 122 and 124 and the jaws 140 move upward and horizontally inward and the arms 126 and 128 and the jaw 170 move downward such that the implant 200 may be released from the implant insertion device 500. When the jaws 140 and the jaw 170 are in their disengaged position, the leg interfaces 146 of the jaws 140 no longer abut the legs 230 of the implant 200, resulting in the release of the tension between the implant 200 and the jaws 140 and a release of the implant 200 from the implant insertion device 500.

In the event the implant 200 remains engaged with the jaws 140 after the jaws 140 and the jaw 170 have moved from their engaged position to the disengaged position, the implant 200 may be removed from the implant insertion device 500 by applying a twisting force. In particular, if the implant 200 remains engaged with either the bridge channel 143 of the jaws 140 or the bridge channel 173 of the jaw 170, applying a twisting force to the implant insertion device 500 removes the implant 200 therefrom. The twisting or rotational force overcomes the force the bridge channel 143 or the bridge channel 173 applies against the implant 200. As a result, the bridge channel 143 or the bridge channel 173 separates from the implant 200, thereby releasing the implant 200 from the implant insertion device 10.

After the implant 200 is removed from the implant insertion device 500, the implant 200 is tamped down to fully engage the tissue or bone. Once fully engaged, the implant 200 moves from its second shape 202 to its first final shape 201, thereby releasing its mechanical energy into the tissue or bone. As the implant 200 moves from its second shape 202 to its first final shape 201, the implant 200 places a constant force on the tissue or bones that fuses the tissue or bone together and aids the healing process.

The design of the implant insertion device 500 allows a gradual release of the implant 200. In particular, if the surgeon presses actuators 133 quickly, then the slider 130 moves from its locked to its unlocked position quickly and the jaws 140 and the jaw 170 move from their engaged position to their disengaged position quickly thereby rapidly releasing the implant 200. On the other hand, if the surgeon believes a patient has poor bone quality, the surgeon can slowly press the actuators 133, which slowly moves the slider 130 from the locked to the unlocked position. Slowly moving the slider 130 from the locked to the unlocked position allows the jaws 140 and the jaw 170 to slowly move from their engaged position to their disengaged position thereby gradually releasing the implant 200.

Although the present invention has been described in terms of the foregoing preferred embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:

1. An implant insertion device adapted for use with a shape memory implant movable between a first shape and a second shape, whereby the implant insertion device maintains the shape memory implant in the second shape until the delivery of the shape memory implant into tissue or bone, the implant insertion device, comprising:
   (i) a body, comprising:
      a first jaw adapted to engage the shape memory implant,
      a second jaw adapted to engage the shape memory implant, and
      a third jaw adapted to engage the shape memory implant, wherein the first, second, and third jaws are movable from a disengaged position to an engaged position; and
   (ii) a slider coupled with the body, wherein the slider is movable between an unlocked position and a locked position, further wherein the slider in its locked position maintains the first, second, and third jaws in their engaged positions, whereby the slider inserts between the first jaw and the second jaw to maintain the first and second jaws in their engaged positions, further whereby the slider engages the third jaw to maintain the third jaw in its engaged position with the first and second jaws such that the first, second, and third jaws engage and maintain the shape memory implant in its second shape.

2. The implant insertion device according to claim 1, wherein the body, further comprises:
   a first arm, wherein the first jaw is at the termination of the first arm;
   a second arm, wherein the second jaw is at the termination of a second arm; and
   a third arm and a fourth arm, wherein the third jaw is at the termination of the third and fourth arms.

3. The implant insertion device according to claim 2, wherein the first jaw and the first arm experience a rotation relative to the body and the second jaw and the second arm experience a rotation relative to the body when the slider is moved from its unlocked to its locked position.

4. The implant insertion device according to claim 2, wherein:
   the first arm maintains the first jaw canted downward when the slider resides in its unlocked position; and
   the second arm maintains the second jaw canted downward when the slider resides in its unlocked position.

5. The implant insertion device according to claim 2, wherein the first arm is shorter in length than the second arm such that the implant insertion device is adapted to receive a shape memory implant with a first bridge at a height different from a second bridge.

6. The implant insertion device according to claim 2, wherein the first arm includes a length substantially the same as the second arm such that the implant insertion device is adapted to receive a shape memory implant with a bridge disposed in a single plane.

7. The implant insertion device according to claim 1, wherein, after the implant insertion device delivers the shape memory implant into tissue or bone, movement of the slider from its locked position to its unlocked position releases the slider from the first, second, and third jaws, further wherein the first, second, and third jaws move from their engaged positions to their disengaged positions such that the first, second, and third jaws disengage from the shape memory implant, thereby releasing the shape memory implant and allowing the shape memory implant to move from its second shape to its first shape.

8. The implant insertion device of claim 1, wherein movement of the first and second jaws to the disengaged position further results in rotation of the first and second jaws away from the shape memory implant.

9. The implant insertion device according to claim 1, wherein the third jaw abuts the first and second jaws and a portion of the third jaw inserts between the first and second jaws when the first, second, and third jaws reside in their engaged positions.

10. The implant insertion device according to claim 1, wherein the implant insertion device is adapted to deliver the shape memory implant into tissue or bone.

11. An implant insertion device adapted for use with a shape memory implant movable between a first shape and a second shape, whereby the implant insertion device maintains the shape memory implant in the second shape until the delivery of the shape memory implant into tissue or bone, the implant insertion device, comprising:
   (i) a body, comprising:
      a first jaw adapted to engage the shape memory implant,
      a second jaw adapted to engage the shape memory implant, and
      a third jaw adapted to engage the shape memory implant, wherein the first, second, and third jaws are movable from a disengaged position to an engaged position; and
   (ii) a slider coupled with the body, wherein the slider is movable between an unlocked position and a locked position, further wherein movement of the slider to its locked position maintains the first, second, and third jaws in their engaged positions and further inserts the slider between the first and second jaws and moves the first and second jaws horizontally outward and in an upward arc to their engaged positions such that the first and second jaws engage the shape memory implant and maintain the shape memory implant in the second shape.

12. An implant insertion device adapted for use with a shape memory implant movable between a first shape and a second shape, whereby the implant insertion device maintains the shape memory implant in the second shape until the delivery of the shape memory implant into tissue or bone, the implant insertion device, comprising:
   (i) a body, comprising:
      a first arm terminating in a first jaw adapted to engage the shape memory implant, wherein the first arm and the first jaw define a first channel,
      a second arm terminating in a second jaw adapted to engage the shape memory implant, wherein the second arm and the second jaw define a second channel, and
      a third arm and a fourth arm terminating in a third jaw adapted to engage the shape memory implant, wherein the third and fourth arms and the third jaw define a third channel, further wherein the first, second, and third jaws are movable from a disengaged position to an engaged position, whereby the first, second, and third channels engage at least a portion of a bridge of the shape memory implant; and
   (ii) a slider coupled with the body, wherein the slider is movable between an unlocked position and a locked position, further wherein the slider in its locked position maintains the first, second, and third jaws in their engaged positions.

13. The implant insertion device according to claim 12, wherein:
the first jaw comprises a tooth having a leg interface that abuts a first leg of the shape memory implant when the first jaw resides in its engaged position; and
the second jaw comprises a tooth having a leg interface that abuts a second leg of the shape memory implant when the second jaw resides in its engaged position.

14. The implant insertion device according to claim 13, wherein the third jaw abuts the first and second jaws when the first, second, and third jaws reside in their engaged positions, further wherein the third jaw includes a tooth that inserts between the tooth of the first jaw and the tooth of the second jaw such that the tooth of the third jaw maintains the first jaw separated from the second jaw.

15. An implant insertion device adapted for use with a shape memory implant movable between a first shape and a second shape, whereby the implant insertion device maintains the shape memory implant in the second shape until the delivery of the shape memory implant into tissue or bone, the implant insertion device, comprising:
(i) a body, comprising:
a first arm terminating in a first jaw adapted to engage the shape memory implant,
a second arm terminating in a second jaw adapted to engage the shape memory implant,
a third arm and a fourth arm terminating in a third jaw adapted to engage the shape memory implant, wherein the first, second, and third jaws are movable from a disengaged position to an engaged position, and
(ii) a slider coupled with the body and movable between an unlocked position and a locked position that maintains the first, second, and third jaws in their engaged positions, wherein the slider includes a slot adapted to receive therein a slider receiver of the body, thereby coupling the slider with the body between the first and second arms and the third and fourth arms such that the slider remains coupled with the body during movement of the slider between its unlocked and locked positions.

16. The implant insertion device according to claim 15, wherein the slider includes a clasp securable with slider channels in each of the first, second, and third jaws, further wherein the clasp maintains the slider engaged with the first, second, and third jaws when the slider resides in its locked position.

17. An implant insertion device adapted for use with a shape memory implant movable between a first shape and a second shape, whereby the implant insertion device maintains the shape memory implant in the second shape until the delivery of the shape memory implant into tissue or bone, the implant insertion device, comprising:
(i) a body, comprising:
a first jaw adapted to engage the shape memory implant,
a second jaw adapted to engage the shape memory implant, and
a third jaw adapted to engage the shape memory implant, wherein the first, second, and third jaws are movable from a disengaged position to an engaged position; and
(ii) a slider coupled with the body, wherein the slider is movable between an unlocked position and a locked position, further wherein the slider in its locked position maintains the first, second, and third jaws in their engaged positions, whereby the slider inserts between both the first jaw and the second jaw to maintain the first and second jaws in their engaged positions such that the first jaw engages a first leg of the shape memory implant and the second jaw engages a second leg of the shape memory implant, further whereby the slider engages the third jaw to maintain the third jaw in its engaged position with the first and second jaws such that the first, second, and third jaws engage and maintain the shape memory implant in its second shape.

* * * * *